US011141008B2

(12) United States Patent
Hearsch et al.

(10) Patent No.: US 11,141,008 B2
(45) Date of Patent: Oct. 12, 2021

(54) SLEEPING BAG FOR INFANTS AND CHILDREN

(71) Applicant: DEAKIN UNIVERSITY, Geelong (AU)

(72) Inventors: Matthew David Hearsch, St Albans Park (AU); Abbas Zahedi Kouzani, Geelong (AU); Scott Daryl Adams, Geelong (AU); Russell Graeme Oliver, Geelong (AU); Jayanth Kumar Jaya Kumar, Geelong (AU); Kane Merrick Mitchell, Geelong (AU); Nicole Joy Heffer, Geelong (AU); Joshua Luke Steele, Geelong (AU)

(73) Assignee: Smartsnugg IP Pty Ltd, Victoria (AU)

( * ) Notice: Subject to any disclaimer, the term of this patent is extended or adjusted under 35 U.S.C. 154(b) by 0 days.

(21) Appl. No.: 16/079,828

(22) PCT Filed: Feb. 24, 2017

(86) PCT No.: PCT/AU2017/050162
§ 371 (c)(1),
(2) Date: Aug. 24, 2018

(87) PCT Pub. No.: WO2017/143401
PCT Pub. Date: Aug. 31, 2017

(65) Prior Publication Data
US 2019/0069697 A1 Mar. 7, 2019

(30) Foreign Application Priority Data
Feb. 24, 2016 (AU) .............................. 2016900645

(51) Int. Cl.
*A47G 9/08* (2006.01)
*A61B 5/11* (2006.01)
(Continued)

(52) U.S. Cl.
CPC ............ *A47G 9/083* (2013.01); *A61B 5/0024* (2013.01); *A61B 5/01* (2013.01); *A61B 5/11* (2013.01);
(Continued)

(58) Field of Classification Search
CPC .......... A47G 9/083; A61B 5/024; A61B 5/01; A61B 5/11; A61B 5/6887
See application file for complete search history.

(56) References Cited

U.S. PATENT DOCUMENTS 2,651,781 A * 9/1953 Buchholz ............. A47D 15/008
2/69.5
6,139,503 A * 10/2000 Muller ............... A61B 5/02158
600/486
(Continued)

FOREIGN PATENT DOCUMENTS

CN 202068944 U 12/2011
CN 105708255 A 6/2016
(Continued)

OTHER PUBLICATIONS

International Search Report and Written Opinion dated May 3, 2017, in Patent Application No. PCT/AU2017/050162, 21 pages.

*Primary Examiner* — Christopher A Flory
(74) *Attorney, Agent, or Firm* — Davis Wright Tremaine LLP

(57) ABSTRACT

A sleeping bag including an internal bag-temperature sensor located in the sleeping bag to measure an internal air temperature in the sleeping bag, and a movement sensor located in or on the sleeping bag to measure movement of the sleeping bag.

18 Claims, 29 Drawing Sheets

(51) Int. Cl.
*A61B 5/00* (2006.01)
*A61B 5/01* (2006.01)
(52) U.S. Cl.
CPC ...... *A61B 5/6887* (2013.01); *A47G 2200/166* (2013.01)

(56) References Cited

U.S. PATENT DOCUMENTS

| | | | | |
|---|---|---|---|---|
| 6,236,880 | B1* | 5/2001 | Raylman | A61B 6/4057 600/436 |
| 6,450,168 | B1* | 9/2002 | Nguyen | A41D 13/1272 128/869 |
| 6,473,910 | B2* | 11/2002 | Creagan | A41D 13/0056 2/102 |
| 7,142,926 | B2* | 11/2006 | Crawford | H04R 25/606 607/55 |
| 9,044,867 | B2* | 6/2015 | Rothschild | B62B 9/00 |
| 2002/0169439 | A1* | 11/2002 | Flaherty | A61P 3/10 604/891.1 |
| 2003/0068949 | A1* | 4/2003 | Ishii | A43B 7/125 442/239 |
| 2007/0204808 | A1* | 9/2007 | Harada | A01K 13/006 119/850 |
| 2008/0040839 | A1* | 2/2008 | Gordon | A41D 13/0053 2/455 |
| 2008/0142060 | A1* | 6/2008 | Orth | A41D 13/005 135/91 |
| 2009/0064390 | A1* | 3/2009 | Beiring | A41D 27/085 2/80 |
| 2009/0163778 | A1* | 6/2009 | Sommerville | G08B 21/0211 600/301 |
| 2009/0306485 | A1* | 12/2009 | Bell | A61B 5/04085 600/301 |
| 2009/0306539 | A1* | 12/2009 | Woodruff | A61B 5/205 600/561 |
| 2009/0313748 | A1* | 12/2009 | Guedes Lopes Da Fonseca | G06Q 10/06 2/458 |
| 2010/0293715 | A1* | 11/2010 | Sakamoto | A47G 9/0215 5/423 |
| 2011/0221598 | A1* | 9/2011 | Eschler | A61B 5/4818 340/575 |
| 2012/0024833 | A1* | 2/2012 | Klewer | G01K 1/14 219/211 |
| 2012/0157904 | A1* | 6/2012 | Stein | D04H 1/49 602/43 |
| 2012/0190259 | A1* | 7/2012 | Frost | A41D 31/065 442/301 |
| 2013/0001422 | A1* | 1/2013 | Lavon | A61B 5/0205 250/338.1 |
| 2013/0036549 | A1* | 2/2013 | McKlarney | A47G 9/0215 5/413 R |
| 2013/0245414 | A1* | 9/2013 | Andreoni | A61B 5/02438 600/388 |
| 2014/0005573 | A1* | 1/2014 | Burkett | A61B 5/6851 600/585 |
| 2014/0018609 | A1* | 1/2014 | Howard | A47D 15/00 600/28 |
| 2014/0137569 | A1* | 5/2014 | Parish | F25B 21/02 62/3.2 |
| 2015/0148599 | A1* | 5/2015 | Wilson | A61B 1/00124 600/109 |
| 2015/0154847 | A1* | 6/2015 | Oliver | G08B 21/0247 340/686.6 |
| 2015/0320588 | A1* | 11/2015 | Connor | A61F 7/0085 607/107 |
| 2015/0374045 | A1* | 12/2015 | Codner | A61F 7/02 2/455 |
| 2016/0073914 | A1* | 3/2016 | Lapetina | A61B 5/6824 600/384 |
| 2016/0136385 | A1* | 5/2016 | Scorcioni | A47C 21/044 600/26 |
| 2016/0165961 | A1* | 6/2016 | Karp | A47D 15/008 2/69.5 |
| 2016/0174728 | A1* | 6/2016 | Karp | A41B 13/06 5/655 |
| 2016/0261425 | A1* | 9/2016 | Horton | H04L 12/2829 |
| 2017/0043117 | A1* | 2/2017 | Karp | A41B 13/06 |
| 2017/0043118 | A1* | 2/2017 | Karp | A41B 13/06 |
| 2017/0086734 | A1* | 3/2017 | Hyde | A61B 5/6846 |
| 2017/0367917 | A1* | 12/2017 | Donat | G16H 40/67 |
| 2018/0317572 | A1* | 11/2018 | Guttman | A41D 13/005 |

FOREIGN PATENT DOCUMENTS

| | | | | |
|---|---|---|---|---|
| GB | 2522662 A | * | 8/2015 | ........ G01K 13/002 |
| WO | 2012073076 A1 | | 6/2012 | |

* cited by examiner

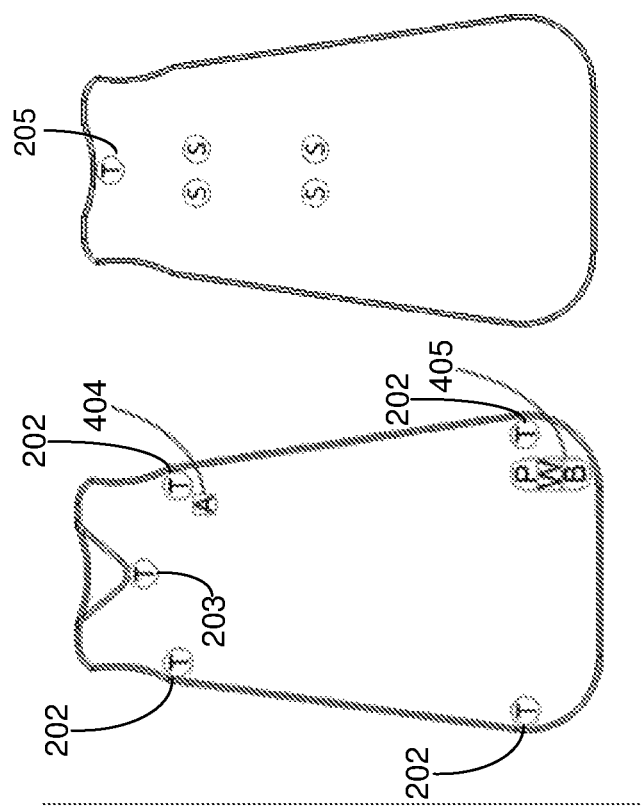
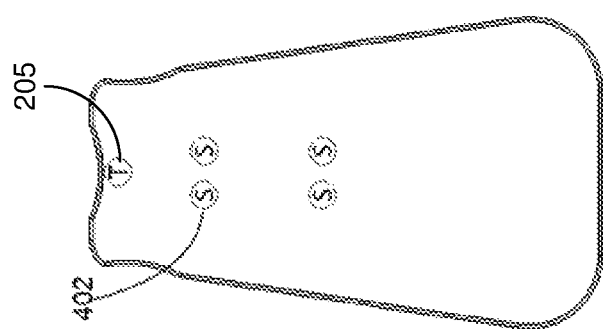
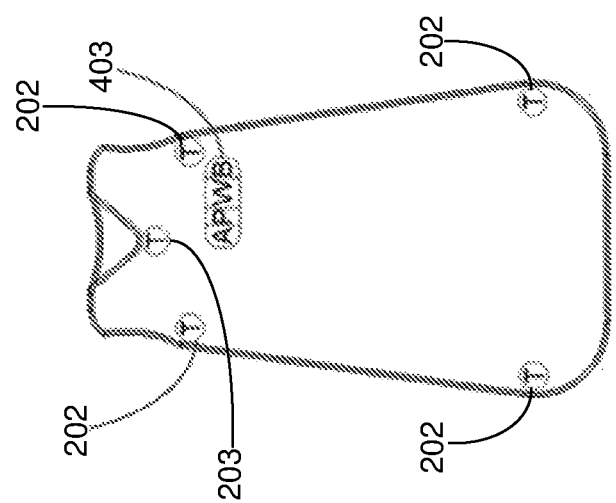
FIG. 5A   FIG. 5B   FIG. 5C   FIG. 5D

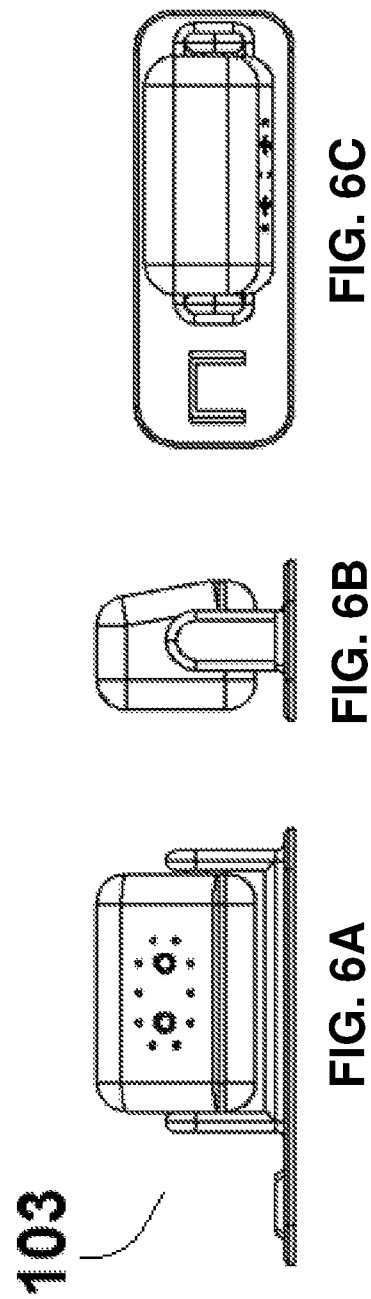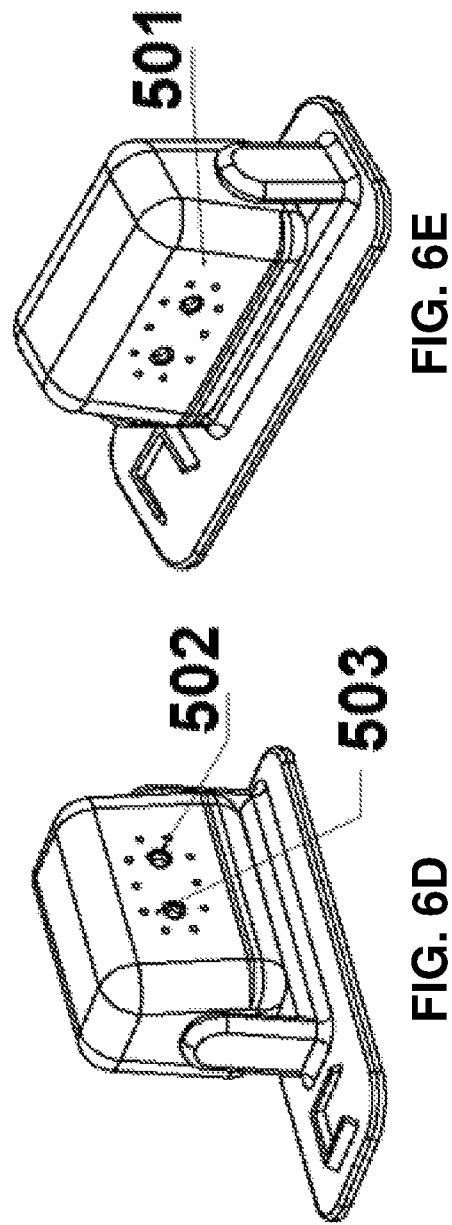

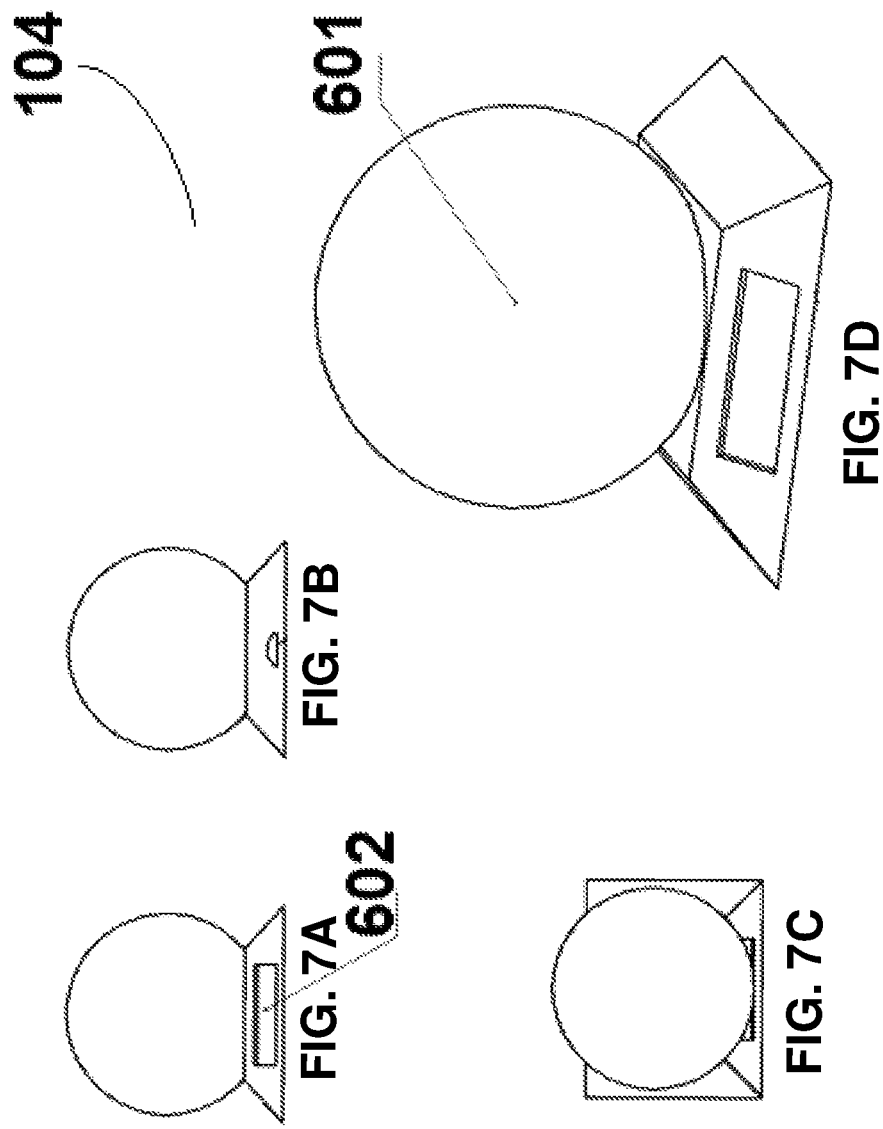

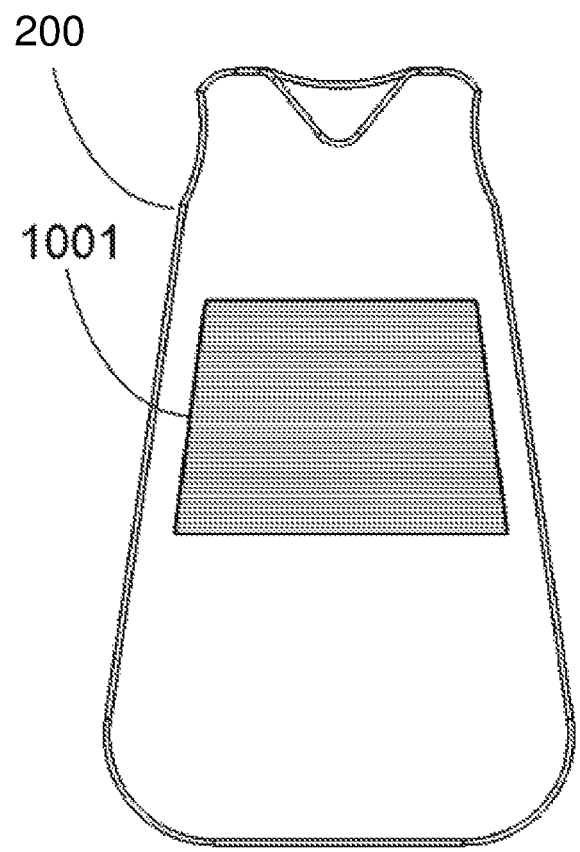
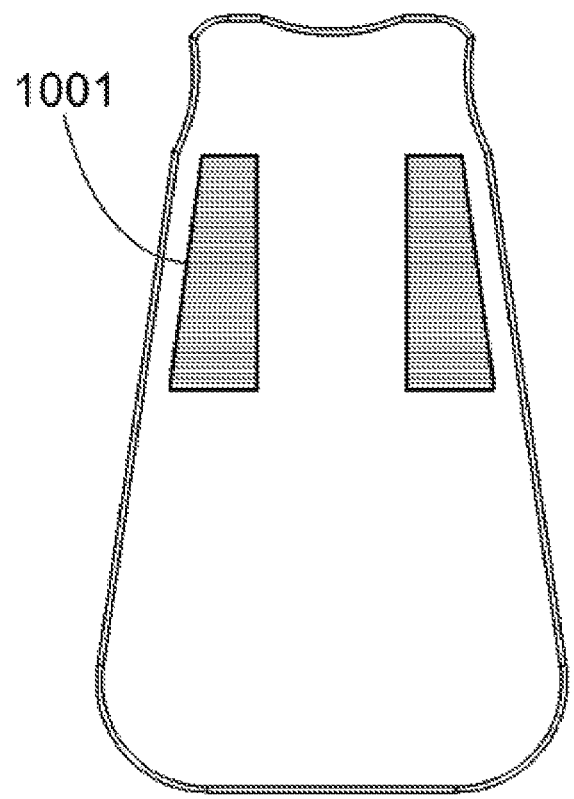
FIG. 11A  FIG. 11B
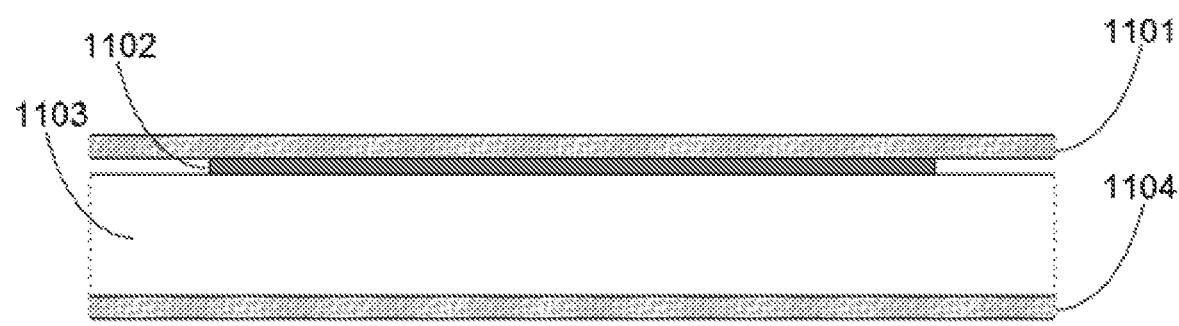
FIG. 12

FIG. 13A
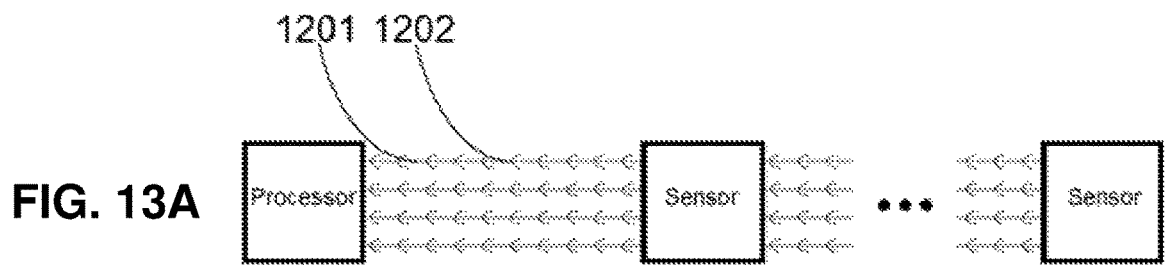
FIG. 13B
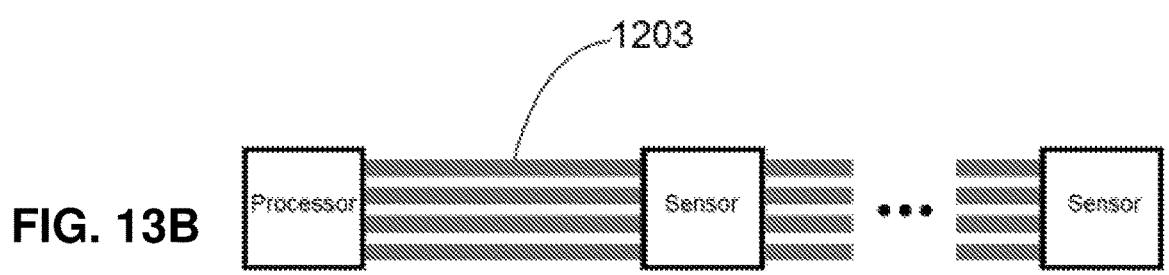
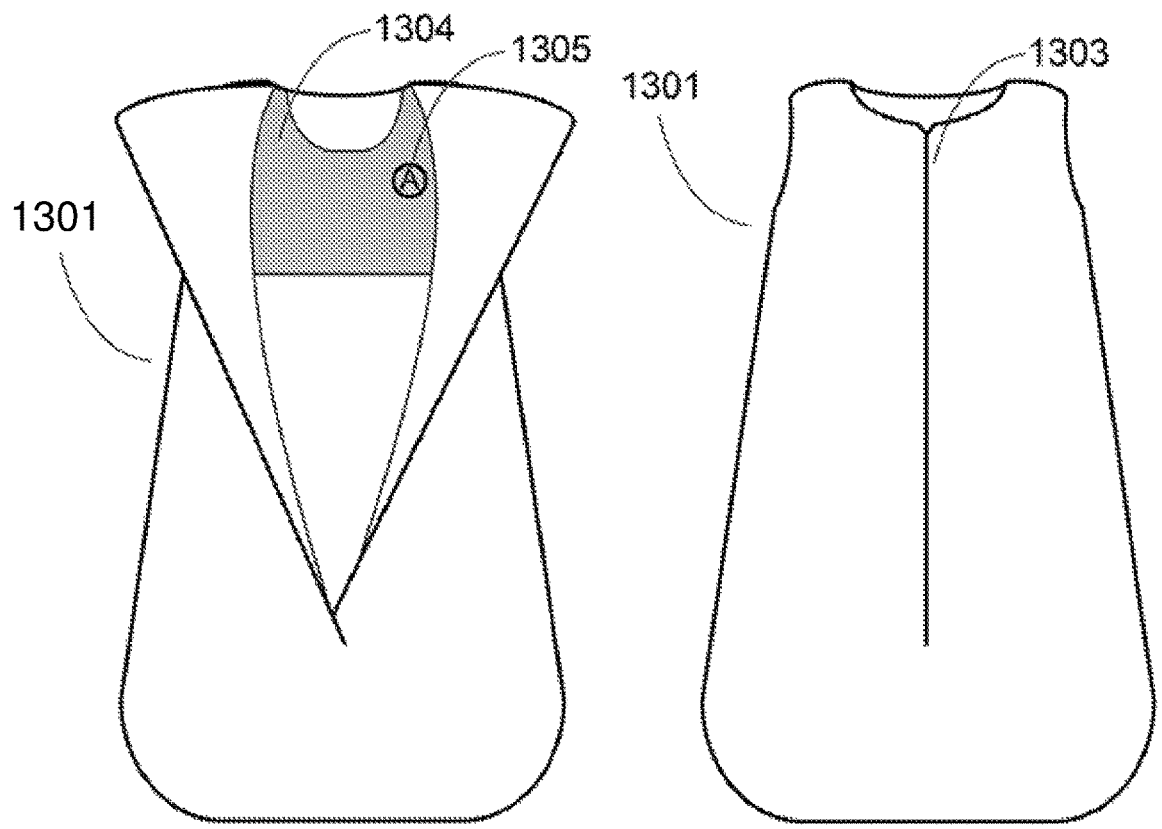
FIG. 14A          FIG. 14B

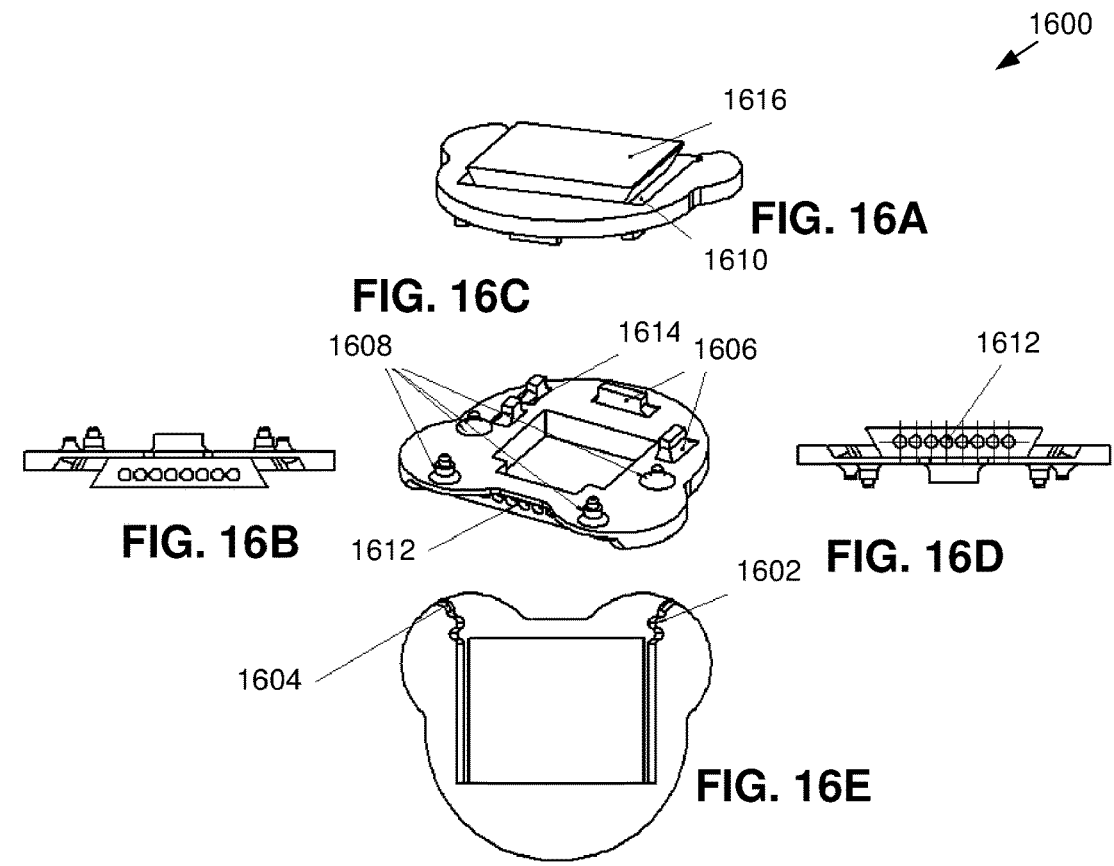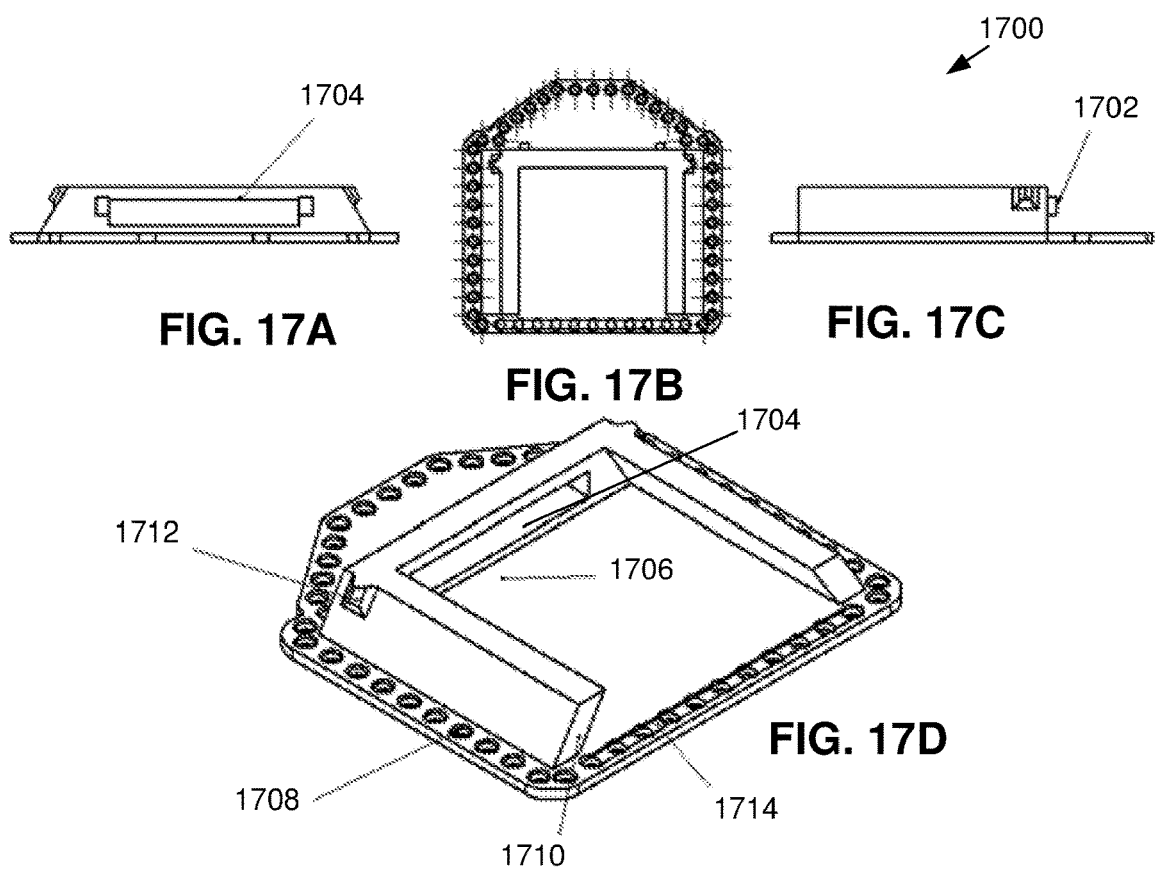

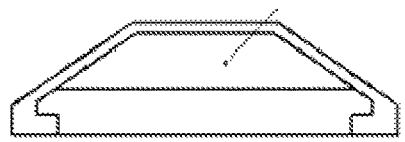
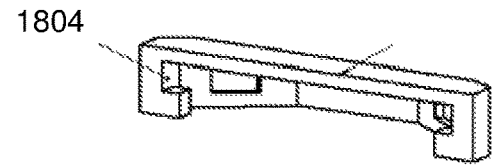
FIG. 18A  FIG. 18B
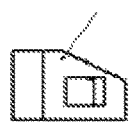
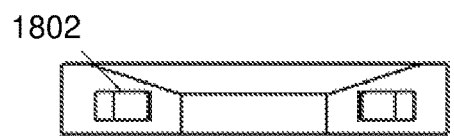
FIG. 18C  FIG. 18D
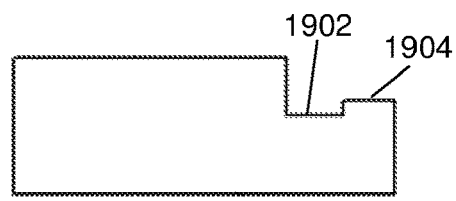
FIG. 19A
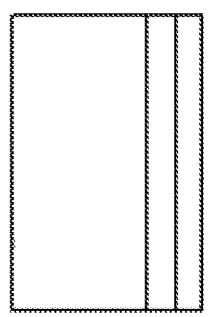
FIG. 19B
FIG. 19C

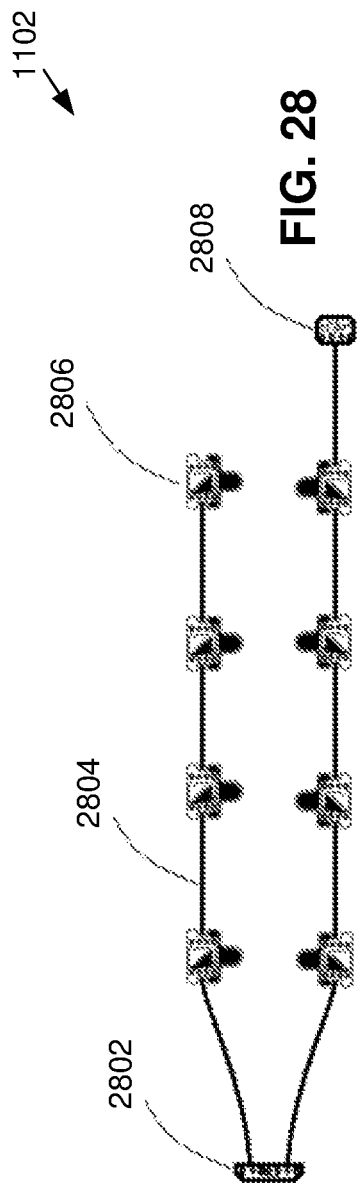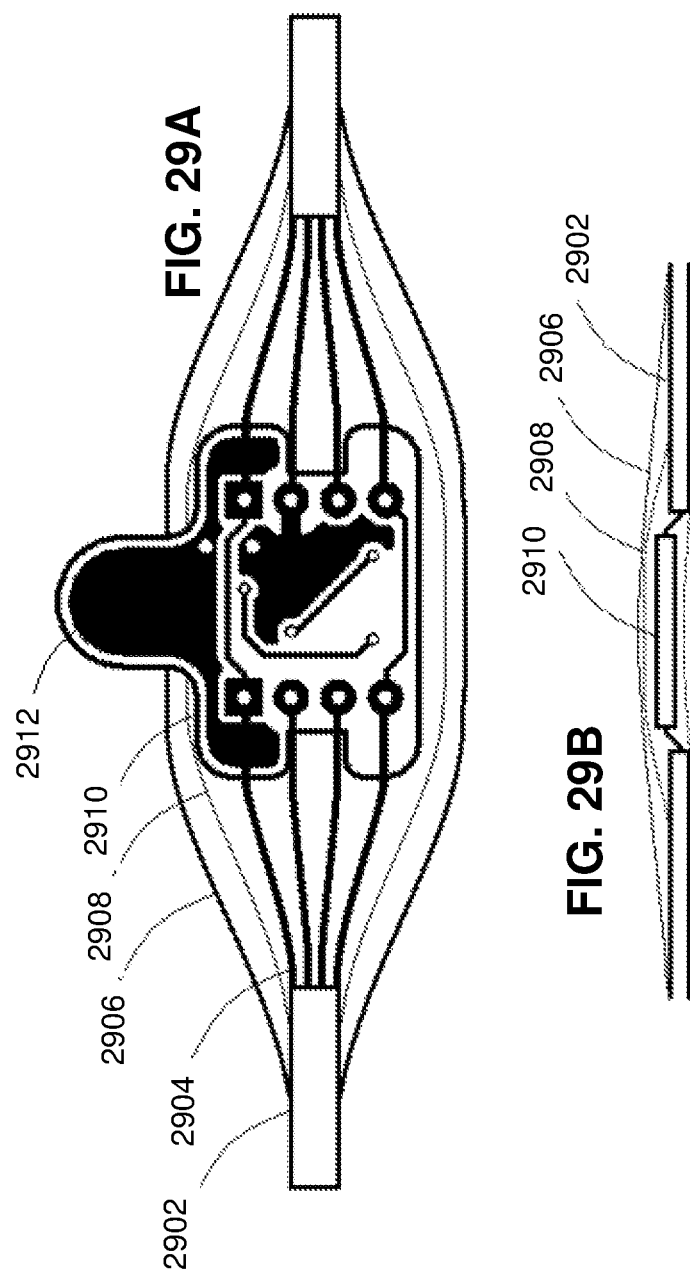

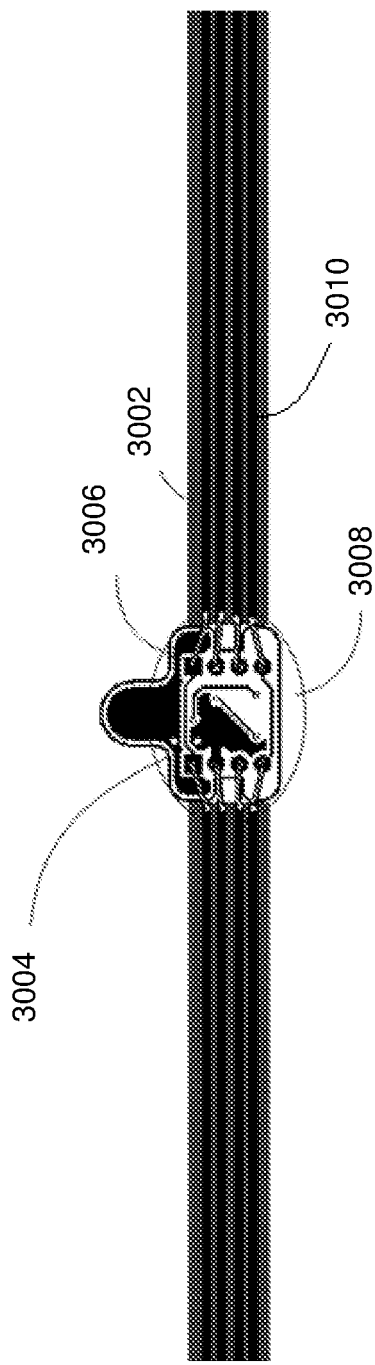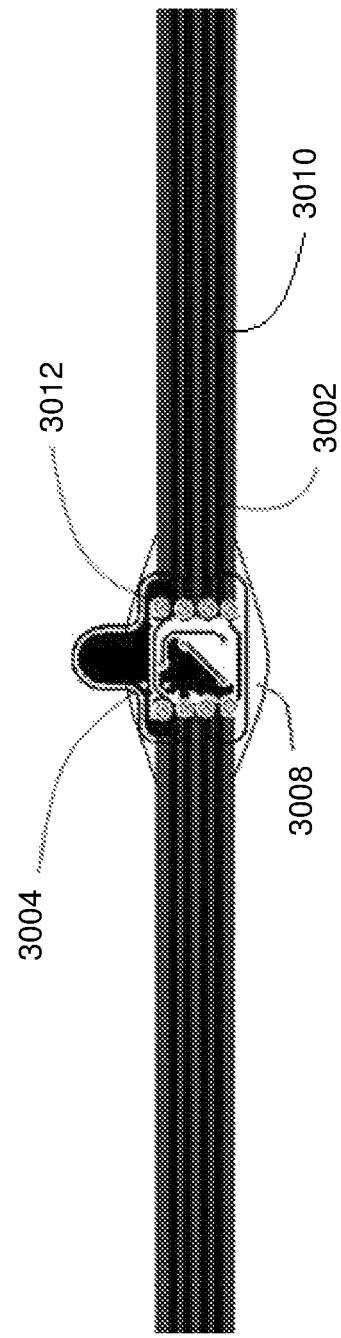
FIG. 30A
FIG. 30B

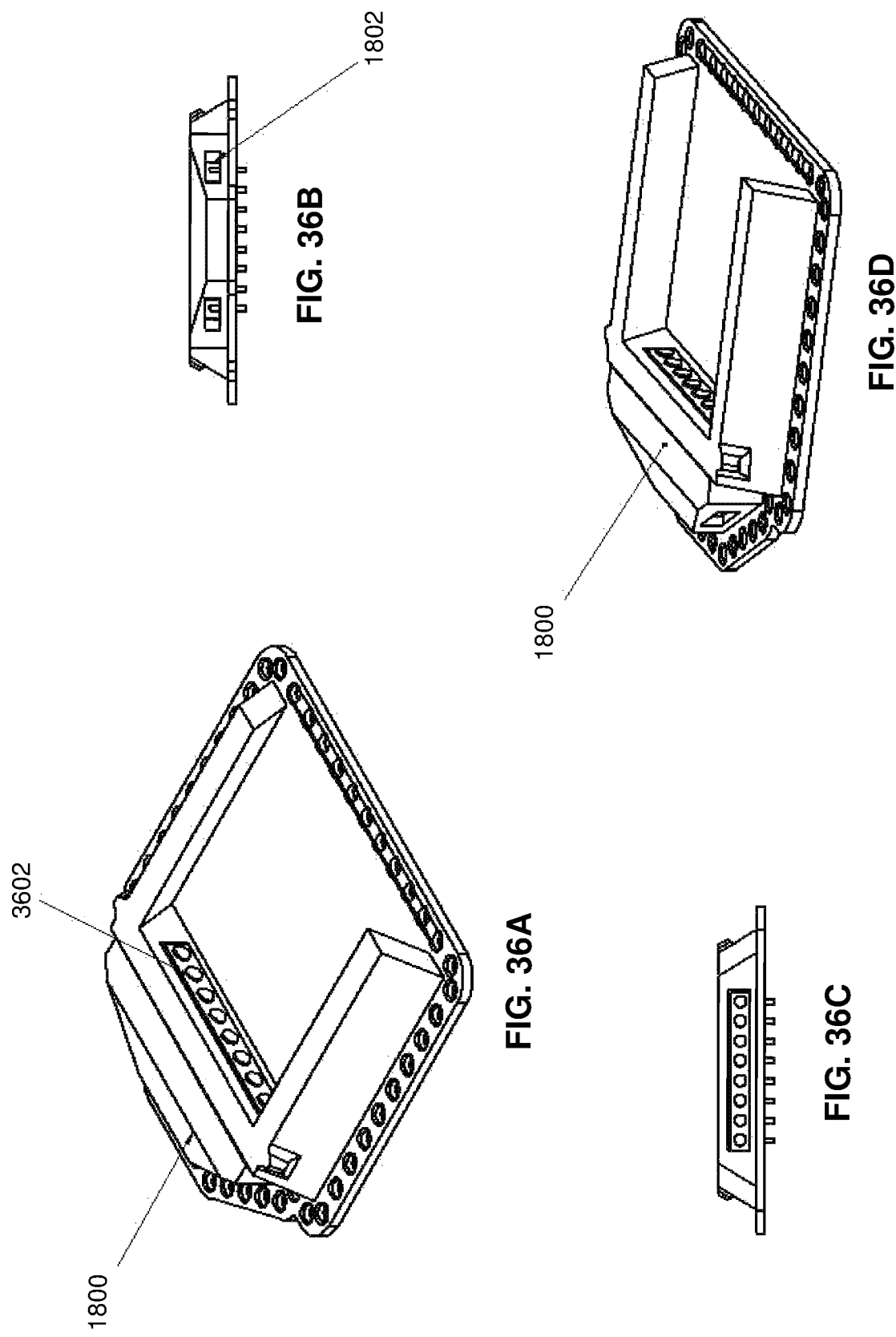

SLEEPING BAG FOR INFANTS AND CHILDREN

TECHNICAL FIELD

The present invention generally relates to sleeping bags for infants and young children, systems including the sleeping bags, methods of manufacturing and using the sleeping bags, on-bag processors, and temperature sensor assemblies.

BACKGROUND

A sleeping bag for children (including infants) is generally an insulated textile bag-like garment used to provide a comfortable, controlled sleeping environment for infants (also referred to as babies) and young children (referred to as "occupants"). Such a sleeping bag may be referred to as a baby sleeping bag. A baby sleeping bag is generally designed to reduce the risk of sudden unexpected death in infancy (SUDI) by removing or reducing the need for blankets or other coverings that could cover the child's head in the sleeping environment.

However, existing baby sleeping bags may fail to adequately address comfort and/or safety concerns for the children, including overheating and/or other risk factors for SUDI, and/or a desire to leave sleeping children undisturbed.

General remote monitoring systems, e.g., baby monitors, may be used by carers (including parents) to monitor sleeping children without disturbing them; however, existing monitoring systems are insufficiently sensitive and/or informative, at least in some situations.

It is desired to address or at least mitigate one or more problems or deficiencies in the prior art, e.g., as set out above, or to at least provide a useful alternative.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY

In accordance with the present invention there is provided a sleeping bag including:
an internal bag-temperature sensor located in the sleeping bag to measure an internal air temperature in the sleeping bag; and
a movement sensor located in or on the sleeping bag to measure movement of the sleeping bag.

The present invention also provides a system including:
the sleeping bag above; and
a base station that communicates electronically with the bag, and processes data from the sensors.

The present invention also provides a method of manufacturing the sleeping bag above, the method including:
selecting locations for the sensors; and
locating the sensors in the selected locations.

The present invention also provides a method of using the sleeping bag above, the method including using the sensors.

The present invention also provides an on-bag processor for a sleeping bag, the on-bag processor including:
a removable portion that processes signals from the sleeping bag; and an attached portion, attached to the bag, that removably receives the removable portion.

The present invention also provides a temperature sensor assembly for a sleeping bag, the temperature sensor assembly including:
a thermally conductive extension that protrudes from a waterproofing layer of the temperature sensor assembly.

BRIEF DESCRIPTION OF THE DRAWINGS

Some embodiments of the present invention are described hereinafter with reference to the accompanying drawings, in which:

FIGS. 6A-6E are diagrams of a base station of the system;

FIGS. 7A-7D are diagrams of a notification station of the system;

FIGS. 11A and 11B are front and back diagrams of the sleeping bag with vents;

FIG. 12 is a cross-sectional diagram of the sleeping bag;

FIGS. 13A and 13B are diagrams of circuitry in the sleeping bag;

FIGS. 14A and 14B are front and back diagrams of the sleeping bag with a singlet;

FIGS. 16A-16E are diagrams of a tag back of the tag;

FIGS. 17A-17D are diagrams of a tag slot of the tag;

FIGS. 18A-18D are diagrams of a slot cover of the tag;

FIGS. 19A-19C are diagrams of a step block of the tag;

FIG. 28 is diagram of a loom assembly of the system;

FIGS. 29A and 29B are diagrams of a sensor printed circuit board (PCB) of the loom assembly;

FIGS. 30A and 30B are diagrams of conductive textiles terminated on the sensor PCB;

FIG. 36 is a diagram of the tag slot with conductive connectors in place.

DETAILED DESCRIPTION

Overview

Figure 1:
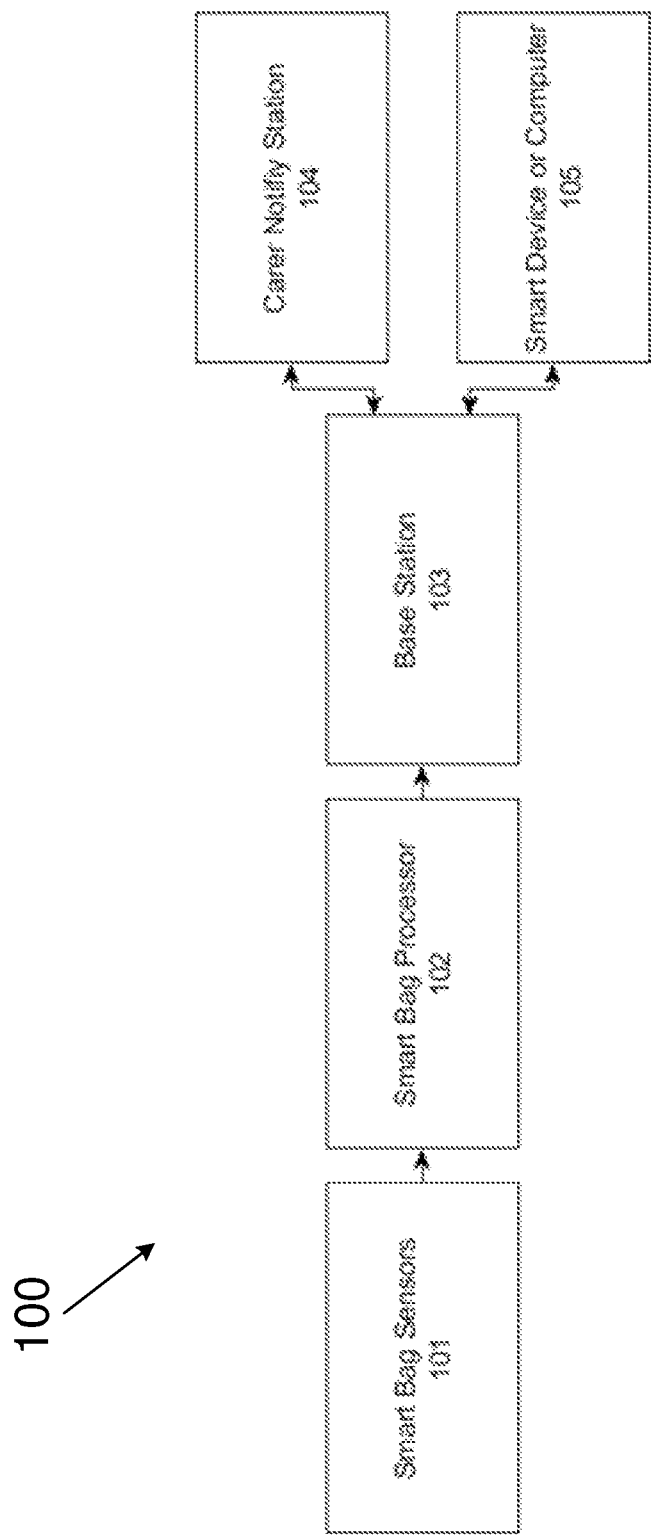
FIG. 1 is a block diagram of a system including a sleeping bag.

Described herein is a sleeping bag that can include a skin-temperature sensor located in the bag to measure a skin temperature of an occupant in the bag.

The bag can include an internal bag-temperature sensor located in the bag to measure an internal air temperature (also referred to as "ambient bag temperature") in the bag.

The bag can include a heart-rate sensor located in the bag to monitor a heart rate of the occupant.

The bag can include a respiration-rate sensor located in or on the bag to monitor a respiration rate of the occupant.

The bag can include a room-temperature sensor located on the bag to measure an ambient room temperature of a surrounding environment.

The bag can include a bag-orientation sensor located in or on the bag to measure an orientation of the bag. The bag-orientation sensor can be an accelerometer and/or a combination of strain sensors.

The bag can include a movement sensor located in or on the bag to measure movement of the bag. The movement sensor can be an accelerometer and/or a combination of strain sensors.

The bag can include electronic circuitry for the sensor(s), wherein the circuitry is located in the bag. The circuitry can include conductive textiles and/or insulated wire. The insulated wire can have a relatively small gauge to provide flexibility. The circuitry and the sensor(s) can be formed of materials that remain operational after washing (in a washing machine) with water.

The bag can include a wireless transmitter to transmit signals representing the measurements from the sensor(s) to a wireless receiver, which can be a commercially available wireless receiver operating according to a communications standard, e.g., for wireless personal area networks, including Wi-Fi communications, infrared communications, cellphone data communications, Bluetooth communications, ZigBee communications, and/or radio-frequency (RF) communications. The transmitter unit may be placed in any location on the exterior of the bag; however for safety, it can be placed remotely from the occupant's head and chest, e.g., on a foot area.

Described herein is a system including:
a. the bag; and
b. a notification station to communicate electronically with the bag, wherein the notification station can include visual indicators and/or audible indicators for providing visible responses and/or audible responses to data representing measurements from the sensor(s).

The system can include a base station to communicate electronically with the bag, and to process data from the sensors.

The system can generate one or more alerts for a carer when:
a. the system determines that the skin temperature of the occupant is too high or low based on a comparison to one or more predetermined skin-temperature levels;
b. the system determines that the internal temperature of the bag is too high or low based on a comparison to one or more predetermined bag-temperature levels;
c. the system determines that the room temperature around the bag is too high or low based on a comparison to one or more predetermined room-temperature levels;
d. the system determines that the heart rate of the occupant is too high or low based on a comparison to one or more predetermined heart-rate levels;
e. the system determines that the respiration rate of the occupant is too high or low based on a comparison to one or more predetermined respiration-rate levels; and
f. the system determines that the occupant is in an unsafe position (e.g., on side or on stomach) based on processing data representing the movement or orientation measurements.

The bag can include adjustable vents to control air flow between an interior of the bag and the surrounding environment. The vents can include mesh. The vents are integrated into the bag. The vents can be referred to as "cooling vents".

The bag can include:
a. an accelerometer for sensing the heart rate and/or the respiration rate; and/or
b. a singlet for pressing the accelerometer onto the occupant.

The singlet can be integrated into the sleeping bag, including by sewing the singlet into the bag.

Described herein is a method of manufacturing the bag, the method including:
a. selecting a location for the skin-temperature sensor in the bag to measure the skin temperature of an occupant in the bag; and
b. locating the skin-temperature sensor in the selected location by attaching the skin-temperature sensor to fabric of the bag.

The manufacturing method can include selecting respective locations for one or more of the sensors, and locating the sensors by attaching the sensors to the fabric of the bag. Attaching the sensors to the fabric can include integrating the sensors between layers of the bag, including between an inner fabric layer and an insulation layer.

The manufacturing method can include providing the monitoring system to the bag, including by attaching and/or integrating components and circuitry of the monitoring system; and sealing the monitoring system from water using enclosures and/or deposition.

Described herein is a method of using the bag. The method can include measuring the skin temperature of the occupant in the bag using the skin-temperature sensor located in the bag.

The method can include measuring the internal air temperature of the bag using the internal bag-temperature sensor located in the bag.

The method can include measuring the heart rate of the occupant using the heart-rate sensor located in the bag.

The method can include measuring the respiration rate using the respiration-rate sensor located in or on the bag.

The method can include measuring the ambient room temperature of the surrounding environment of the bag (i.e., room air temperature) using the room-temperature sensor located on the bag and/or on the base station.

The method can include measuring the orientation of the bag using the bag orientation sensor located in or on the bag.

The method can include measuring movement of the bag using the movement sensor located in or on the bag.

System

Described herein is a smart sleeping bag for occupants (including young children and infants/babies) that allows carers (e.g., parents) to monitor measurements made by the bag, including one or more of:
a. an ambient internal bag temperature inside the bag;
b. a room temperature (i.e., an ambient temperature of the surrounding environment) outside the bag;
c. a skin temperature of the occupant in the bag;
d. a respiration rate of the occupant;
e. a heart rate of the occupant;
f. an orientation of the bag, and thus an orientation or position of the occupant; and
g. movement of the bag, and thus movement of the occupant.

The bag can include the following materials:
a. an outer fabric layer (also referred to as a "shell"), formed of standard materials, e.g., cotton, silk and/or polyester, that lies around the exterior of the bag;
b. an inner fabric layer (also referred to as a "liner"), formed of standard materials, in the interior of the bag for resting against the occupant; and
c. an insulation layer (also referred to as "fill"), formed of standard materials, e.g., cotton towelling, wool, and/or synthetic padding, between the outer fabric layer and the inner fabric layer.

The bag materials are washable with water, including in a laundry machine.

The bag can have a fitted neck, armholes (or sleeves), and no hood. The bag can comprise one or more front panels and back panels that are joined by side seams and bottom seams.

The bag can include a monitoring system, integrated into the bag, which monitors the occupant and generates signals and data from sensors in the bag that measure values of physical parameters including: the internal bag temperature, the room temperature, the skin temperature, the respiration rate, the heart rate, the position/orientation of the occupant, and the movement of the occupant. The monitoring system can include the sensors and an on-bag processor.

The bag is worn by the occupant such that the physical parameters (including temperature, position, respiration rate, etc.) can be measured while keeping the occupant comfortable and unharmed.

The bag makes the measurements using the sensors (which can be referred to as "sensing devices"), which each gather the measurements, and each generate electronic signals representing the measurements for communication to the on-bag processor which is at least one electronic data-processing apparatus on or in the bag. The on-bag processor can be referred to as a "tag" or "processing device". The on-bag processor can be based on commercially available data processors, or on custom-made components running a custom program and utilizing custom circuitry. The on-bag processor can be produced through a commercially available Printed Circuit Board fabrication process. The on-bag processor performs one or more analysis processes using received raw sensor data from the sensors, and generates (from the analysis processes, e.g., compression for transmission) gathered data for a carer notification station (e.g., a device), or the base station, or a monitoring application in a computer or smart phone (referred to as a "smart device"). The on-bag processor communicates electronically with an on-bag communications component, also part of the monitoring system, that can communicate wirelessly with an external processing device (referred to as a "base station") which can facilitate longer term data storage and more analysis processes than the on-bag processor alone.

The on-bag processor can include:
a. a battery for powering the other components of the monitoring system;
b. a charging connection for recharging the battery; and
c. sealed enclosures, including boxes and/or packaging, for sealing the other components of the monitoring system against water, moisture, and dust, allowing the bag to be washed with water and soap, including in a washing machine.

The internal (or "in-bag") temperature sensor can include a thermistor, a thermocouple, and/or a complementary metal-oxide semiconductor (CMOS)-based temperature-sensing chip. Thermistors and thermocouples report the temperature of the ambient environment by altering a measurable parameter (e.g., resistance or current) in a repeatable manner in response to a change in temperature. A CMOS-based temperature sensor is an electronic chip which integrates a thermistor/thermocouple as well as a digital analogue converter to report the temperature measurements as digital data. The bag can include a plurality of in-bag temperature sensors in a plurality of different locations in the bag: for an in-bag temperature that differs in different locations in the bag, measurements from the plurality of in-bag sensors can be combined to provide more accurate in-bag temperature measurements.

The room temperature sensor can include a thermistor, a thermocouple, and/or a complementary metal-oxide semiconductor (CMOS)-based temperature sensing chip. The bag can include a plurality of room temperature sensors in a plurality of different locations on the bag (the room temperature sensors are not in the bag): for a room temperature that differs in different locations around the bag, e.g., under the bag and above the bag, measurements from the plurality of room sensors can be combined to provide more accurate room temperature measurements. Alternatively or additionally, the system can include one or more room temperature sensors in the base station, which is located in the room with the sleeping bag. Accurate data representing the current ambient temperature in the room can be used to control heating or cooling systems, either manually or automatically, in order to create a comfortable environment for the child.

The skin temperature sensor can include a thermistor, a thermocouple, and/or a complementary metal-oxide semiconductor (CMOS)-based temperature sensing chip. The skin temperature sensor can be integrated into the bag, including into an insert (including a collar, a body strap and/or a singlet) in the sleeping bag that is located in physical contact with the occupant's skin.

The respiration rate sensors (also known as "respiration sensors") can include one or more strain/pressure sensors or accelerometers. Strain/pressure sensors include sensitive flexible sensor elements integrated into the bag, including using conductive textiles. As the occupant breathes in and out, corresponding movements are experienced by the sensors. Through respiration data processing (including signal filtering), sensed movements due to respiration can be isolated from other sensed movements and other pressure signals, and thus the respiration rate can be measured. The strain/pressure sensors can include piezoelectric sensors, resistive sensors or capacitive sensors to measure the respiration. The accelerometer can be secured at a fixed location, including on or adjacent to a chest of the occupant, and the accelerometer detects acceleration changes due to inhalation and exhalation; the measured acceleration due to respiration can be isolated from measured acceleration due to other movements using the data processing mentioned hereinbefore. The respiration sensor can be integrated into the bag, including into an insert (including a collar, a body strap and/or a singlet) in the sleeping bag that is located in physical contact with the occupant's chest.

The heart rate sensor can include one or more strain/pressure sensors or accelerometers, which can be the same sensors as the respiration rate sensors, i.e., at least one strain/pressure or accelerometer can be used as both a respiration-rate sensor and a heart-rate sensor, with the relevant physical parameter measurements being separated in the data processing. Ballistocardiographic data processing based on ballistocardiographic methods, can be used to non-invasively measure cardiovascular function through the vibrations caused by cardiac movement on the surface of the occupant. In the ballistocardiographic processing, the heart rate is estimated from measurements of relatively small movements of the occupant (including ribcage and spine) in response to heart activity.

The bag-orientation sensor can include one or more accelerometers, which can be the same as the heart-rate sensors and/or the respiration rate sensors. The orientation or position of the occupant is used in the system to detect if the occupant is lying on his/her back or chest or side. An accelerometer is an electronic component that measures the acceleration that it experiences, which can include acceleration experienced due to gravity. The bag-orientation sensor is located at a predetermined location in or on the bag, including the back or the front or one of the sides, and a constant component of the measured acceleration can be used to determine the direction of gravity, and thus the orientation of the occupant. For example, if the Z-Axis of the accelerometer is attached to front of the bag facing outwards, and the accelerometer is measuring a negative acceleration in the Z-Axis, the system can estimate, using orientation data processing that the occupant is lying on her/his back. If the Z-Axis is measuring a positive acceleration, the orientation data processing can estimate that the occupant is lying on his/her chest. Through reading the measurement reported by the accelerometer, the orientation of the occupant can be estimated using the orientation data processing.

The on-bag communications component can be configured to communicate with the base station, or directly with a smart device (e.g., smart phone, mobile phone, laptop, notebook, and/or tablet computer, etc.), using standard protocols, including the Wi-Fi, Near Field Communication, Bluetooth or radio frequency identification (RFID) protocols. The on-bag communications component can have a very low level of power consumption, a long transmission range, and be safe for use in close proximity to humans.

The on-bag processor can include a microcontroller to receive and process the raw sensor data. The on-bag processor is a low-power device that is configured to transition to a sleep state when not actively receiving, processing or communicating data, to minimize battery usage. The on-bag processor is configured to read and process the sensor data at a high data rate in order to transform the raw sensor output in real time, e.g., to generate accurate human-legible data. The processing device has data inputs to receive raw data and/or signals directly from one, or a plurality, or all of the sensors (without introducing additional components).

The battery of the monitoring system is rechargeable, and has a capacity to power the monitoring system for a plurality of days of use, e.g., for 8, 10, 12, or 14 hours of use per day. The battery is encased and sealed by a plastic capsule of a size that is safe for use around infants (i.e., too large for swallowing, according to existing safety guidelines), and which electrically isolates the battery from the occupant. The battery capsule is formed in a comfortable shape (i.e., a shape with no sharp edges or corners that could poke or irritate the occupant of the bag) and using materials that are safe for infants and young children to handle or touch, including orally, for example, acrylonitrile butadiene styrene (ABS) plastic. The charging connection for recharging the battery can include a wireless charging connection or a contact-based (or wired) charging connection. The wireless charging connection can allow the battery capsule to be entirely sealed from the surrounding environment with no openable aperture or electrical contact on the battery capsule's exterior. The contact-based charging connection exposes contacts of the battery, directly or indirectly, in a safe and resealable manner to allow for recharging.

The entire monitoring system is packaged in such a way that none of the electrical components is in direct contact with the occupant or the outside environment. The components can be included between textile layers of the bag, or within sealed packaging (which can include a plastic capsule) attached to fabric of the bag. The conductive connections in the monitoring system are selected to have similar flexibility to that of the bag fabric, or at least substantial flexibility to allow natural movement of the occupant and/or washing in a washing machine. The conductive connections can include relatively light gauge wire and/or conductive textiles.

The components of the bag (including the electronic components of the monitoring system) are either removable from the bag, or waterproof and robust enough to allow for simple machine washing. The sensors can be coated in a waterproof material, e.g., silicone or plastic. The coating of waterproof material can be performed by dipping the sensor in the material and/or forming a molded housing to contain the sensor.

The on-bag communications component can include a main transmission unit, and the main transmission unit can be located near to or at a foot end of the bag, which can reduce electromagnetic radiation sources near vital organs of the occupant.

The system can include the monitoring application (also referred to as a "user-facing application") in the smart device, and the application can include a user interface for the carer.

Methods

A method of manufacturing the bag can include:
a. selecting a location for the skin-temperature sensor in the bag to measure the skin temperature of an occupant in the bag; and
b. locating the skin-temperature sensor in the selected location by attaching the skin-temperature sensor to fabric of the bag (by embedding the skin-temperature sensor into the inner layer of the bag).

The manufacturing method can include selecting respective locations for all of the sensors, and locating the sensors by attaching them to the fabric of the bag. Attaching them to the fabric can include integrating them between layers of the bag, including between the inner fabric layer and the insulating layer.

The manufacturing method can include providing components and circuitry of the monitoring system to the fabric of the bag, including by attaching and/or integrating the components and circuitry; and sealing the monitoring system from water using enclosures and/or deposition.

The manufacturing method can include assembly of an enclosure, which can contain the on-bag processor, battery and wireless transceiver. The enclosure can also contain one or more of the bag sensors, such as an accelerometer. The enclosure can be manufactured by 3D printing or injection moulding. The enclosure can be designed to take on the shape of an animal face.

The manufacturing method can include assembly of the base station, including the stand, enclosure and cap. These components of the base station can be manufactured by 3D printing or injection moulding.

A method of using the bag can include measuring the skin temperature of the occupant in the bag using the skin-temperature sensor located in the bag.

The method can include measuring the internal air temperature of the bag using the internal bag-temperature sensor located in the bag.

The method can include measuring the heart rate of the occupant using the heart-rate sensor located in or on the bag.

The method can include measuring the respiration rate of the occupant using the respiration-rate sensor located in or on the bag.

The method can include measuring the ambient room temperature of the surrounding environment of the bag using the room-temperature sensor located on the bag and/or on the base station.

The method can include measuring the orientation of the bag using the bag orientation sensor located in or on the bag.

The method can include measuring movement of the bag using the movement sensor located in or on the bag.

Embodiment

In an embodiment, as shown in FIG. 1, the system is a smart sleeping bag system 100 that can include: the sensors in the form of a plurality of sensors 101; the on-bag processor in the format of an on-bag processor 102 (also referred to as "P" in the drawings); the base station in the form of a base station 103; the notification station in the form of a notification station 104; and the smart device in the form of a smart device 105 (e.g., mobile phone, computer, smart phone, laptop, notebook, tablet computer, etc.) with the user-interface application.

The sensors 101 are implanted into or onto the fabric of the bag in the form of a sleeping bag 200 to detect the physical properties (by measuring the physical parameters) of the occupant and the surrounding environment (inside the bag 200 and outside the bag 200).

The sensors 101 generate electronic signals representing the measurements, and these measurement signals are received and processed by the on-bag processor 102 located in or on the bag fabric. The on-bag processor 102 is also referred to as a "tag" because it is attached like a tag to the bag 200.

The on-bag processor 102 generates information (represented by measurement data) from the sensor signals, and communicates this information to the base station 103 via a low-energy wireless communications protocol, such as Bluetooth low-energy or low-power RF, using a wireless transceiver ("W").

The base station 103 communicates with the connected carer notification station 104 and the smart device 105 through wired or wireless communication connections, including standard computer networks. The base station 103 can transmit data over the Internet to an off-site computer system that provides long-term data analytics and predictions.

The carer notification station 104 and the smart device 105 display information gathered from the bag 200, and/or visual or audible alerts in response to information sent from the base station 103. The displayed information can include performance and/or diagnostic information generated by the base station 103 and/or the bag processor 102.

Figure 2A:
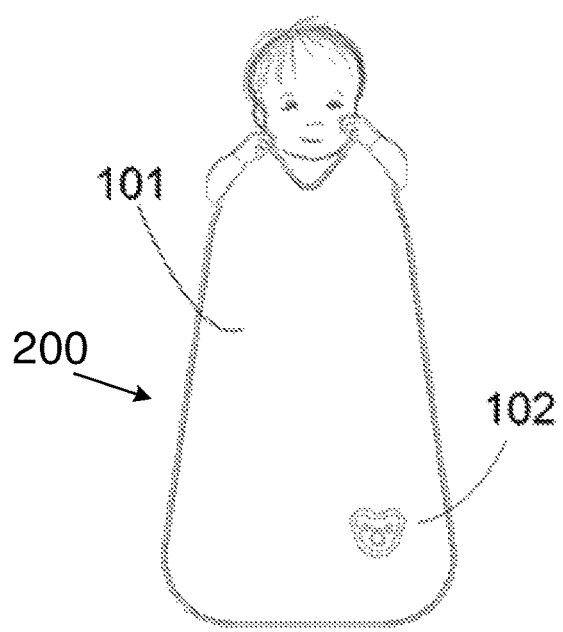
FIGS. 2A-2D are diagrams showing physical components of the system.
Figure 2B:
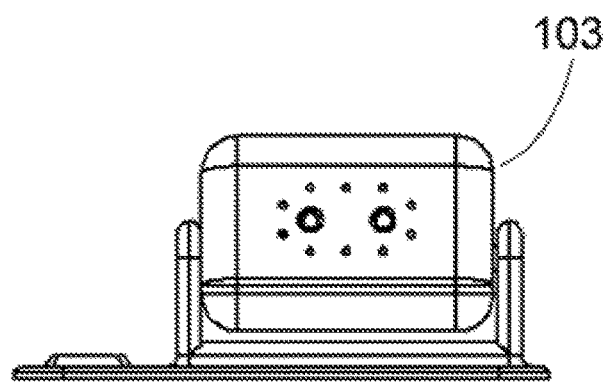
Figure 2C:
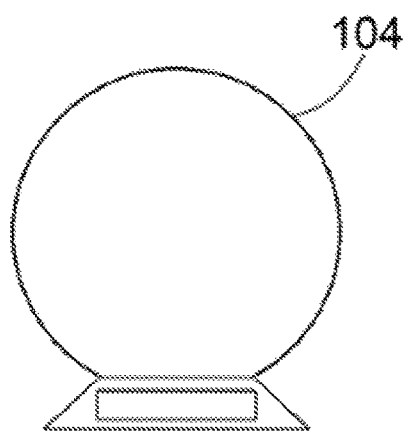
Figure 2D:
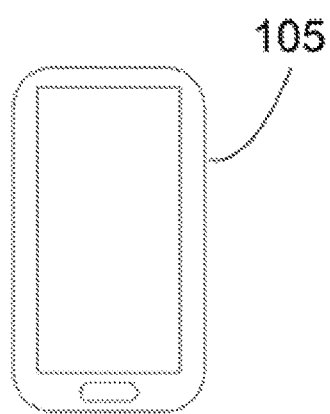

As shown in FIG. 2A, the occupant of the bag 200 is able to freely move their arms and head while wearing the bag 200 while the rest of their body (including torso and legs) is enclosed within the bag 200. The occupant can also move their body and legs inside the bag 200 because it is loose fitting, i.e., not pressed against the body of the occupant. The on-bag processor 102 is located in an enclosure to ensure isolation from the surrounding environment and decrease the danger of swallowing or choking on the device. This enclosure can be removably attached to the exterior of the bag 200 so that it can be removed manually prior to washing. The sensors 101 within the bag 200 can be waterproofed through encasing them in a layer of plastic. The conductive connections in the bag 200 can include washable conductive textiles and/or insulated wiring so that the bag 200 can be washed without substantive damage. As shown in FIGS. 2B to 2D, the base station 103, the carer notification station 104, and the smart device 105 can be separate devices or apparatuses that are configured to communicate electronically.

As shown in FIGS. 3A to 3E, the bag 200 can include a plurality of temperature sensors ("T"), including:
  a. an on-bag room temperature sensor 203 (to measure air temperature of the room) located in the middle top outside of the front of the bag 200, i.e., located on the front of the bag, in the centre of the bag collar or bag neck, i.e., above the sternum or chest of the occupant in his/her normal lying position;
  b. an on-bag skin temperature sensor 205 (to measure the occupant's skin temperature) located in the middle top inside of the back of the bag 200, i.e., located in the back of the bag 200, in the centre of the bag collar or bag neck, i.e., under and touching the back of the occupant's neck in his/her normal lying position; and
  c. a plurality of internal bag temperature sensors 202 (on both sides).

The sensors 101 can be placed in a range of locations throughout the bag. The temperature sensors 202 can provide a full temperature profile of the occupant of the bag. The sensors 202 may be placed around the outer edge of the bag.

The plurality of bag temperature sensors 202 are distributed at different locations in the bag 200, along the height of the bag 200 (i.e., from near the occupant's shoulder to near the occupant's feet) at the sides of the bag 200 (i.e., on the occupant's right side and on the occupant's left side), to gather temperature measurement signals from the locations, including:
  a. seam sensors at or near the seams of the bag 200 to simplify manufacturing and minimize movement experienced by these sensors; and
  b. top sensors and bottom sensors that are at or near the top and bottom of the bag 200 respectively in order to gather measurements spanning the length of the bag 200 of the air temperature within the bag 200 rather than a single point measurement.

The measurements from these temperature sensors 202 can be correlated or processed together to generate a more accurate bag temperature reading from the bag 200 than would be provided by a single sensor at a single location.

Figures 3A, 3B, 3C, 3D:
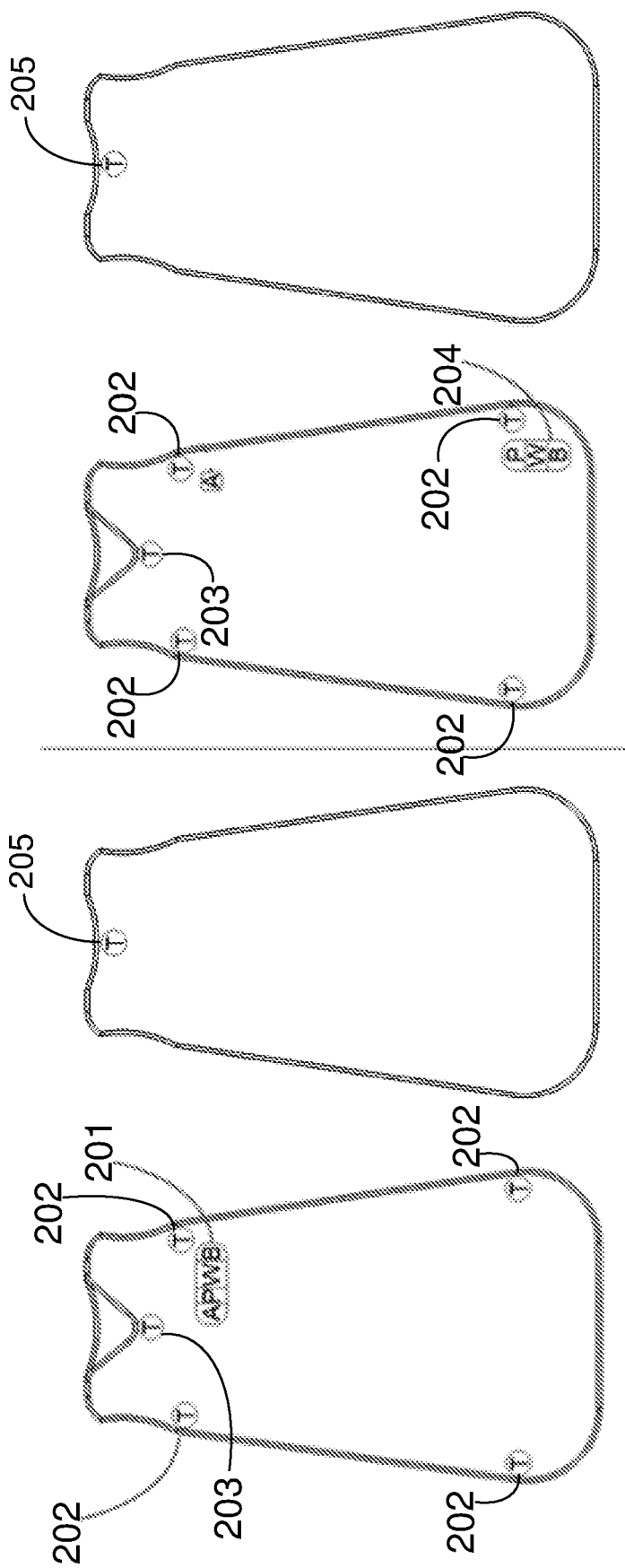
FIGS. 3A-5H are diagrams of sensor locations in/on the sleeping bag.
Figure 3H:
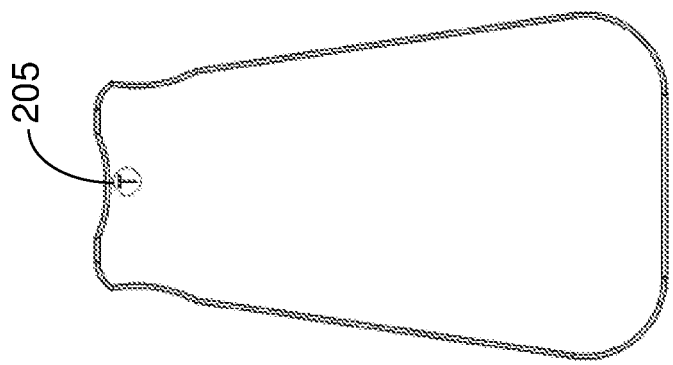

As shown in FIGS. 3A and 3B, in a first configuration, the bag 200 can include an accelerometer ("A") to take measurements of position/orientation, respiration and/or heart rate. This accelerometer "A" is located in a chest area of the bag 200, which is directly above the chest of the occupant. The accelerometer "A" is located above the chest of the occupant within a chest enclosure 201 containing the on-bag processor "P", the wireless transceiver "W" and a battery ("B"), which is a configuration that minimizes wiring required to connect these components.

As shown in FIGS. 3C and 3D, in a second configuration, the on-bag processor "P", wireless transceiver "W" and battery "B" can be located together in a foot enclosure 204 that is located close to the foot of the bag 200, while leaving the accelerometer "A" nearer the chest to make more accurate acceleration measurements than would be provided near the foot end.

Figure 3G:
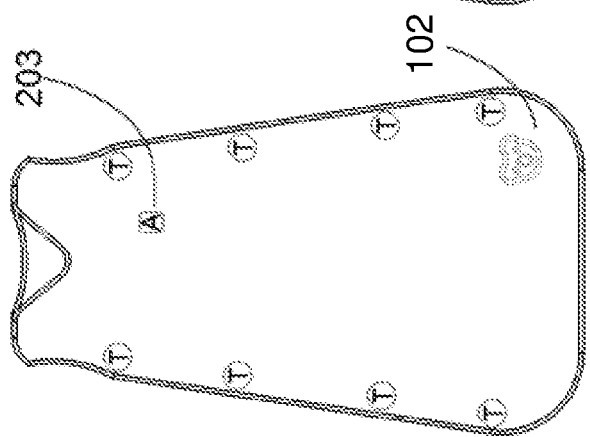
Figure 3F:
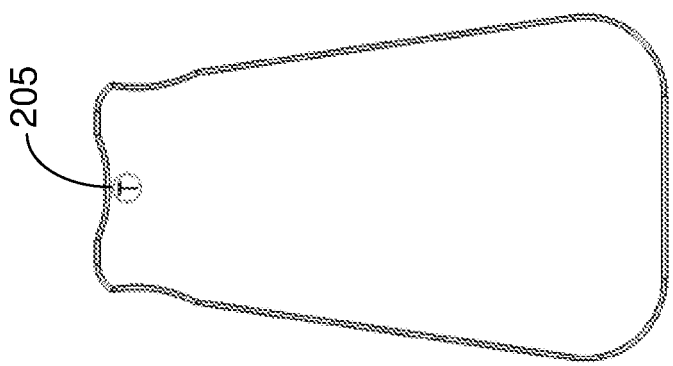
Figure 3E:
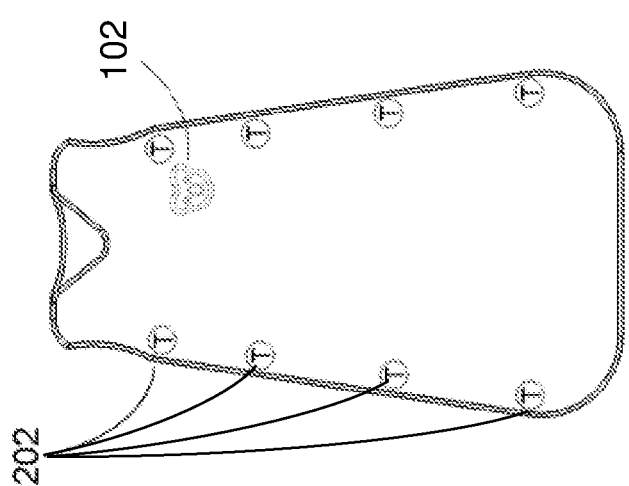

As shown in FIG. 3E, the bag 200 can include the on-bag processor 102 on the bag 200 in the chest area of the bag 200, and the on-bag processor 102 can include the accelerometer, and the on-bag room temperature sensor 203 may be excluded.

As shown in FIG. 3G, the bag 200 can include the on-bag processor 102 on the bag 200 in the foot area of the bag 200, and the accelerometer can still be mounted near the chest area.

Figure 4A:
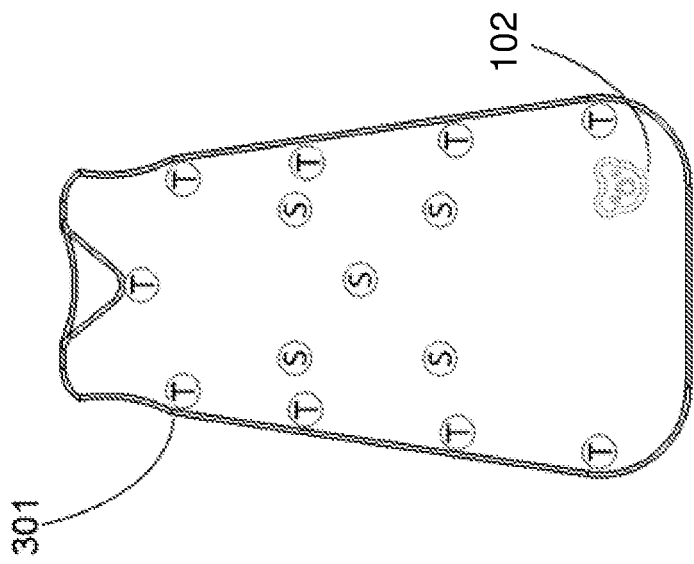
Figure 4B:
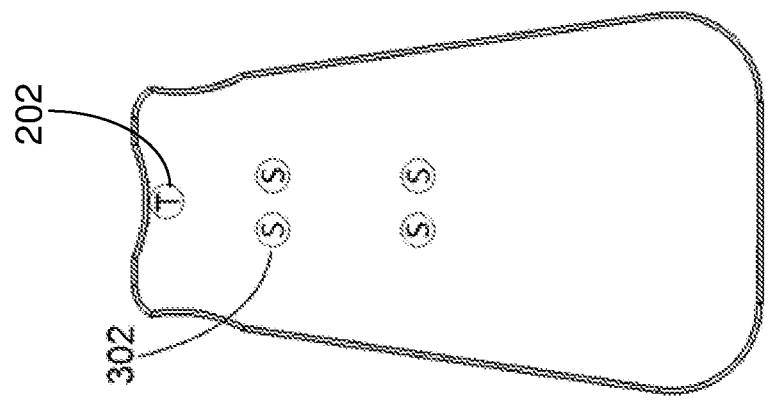
Figure 4C:
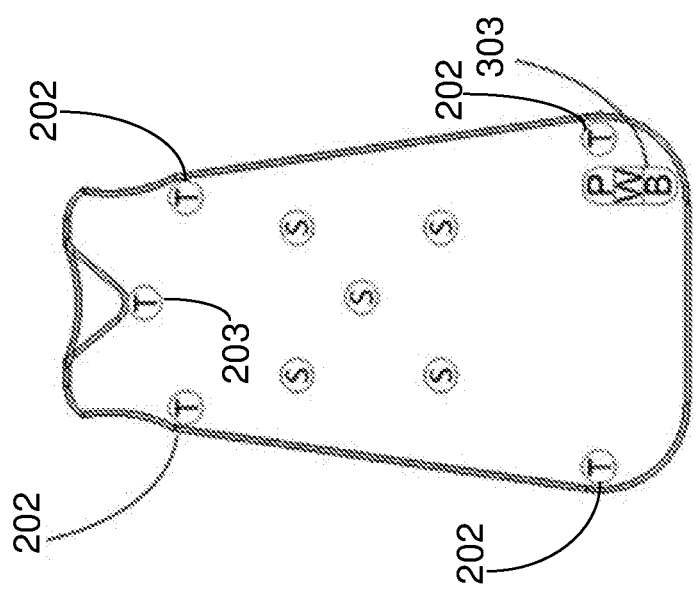
Figure 5H:
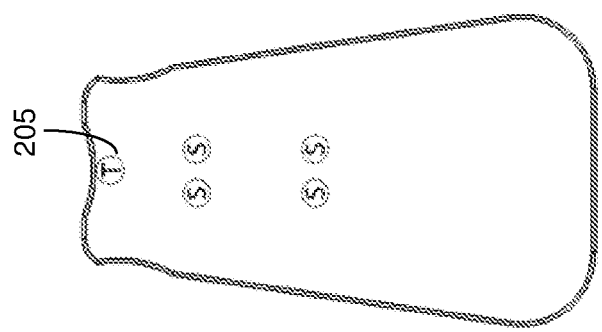
Figure 5G:
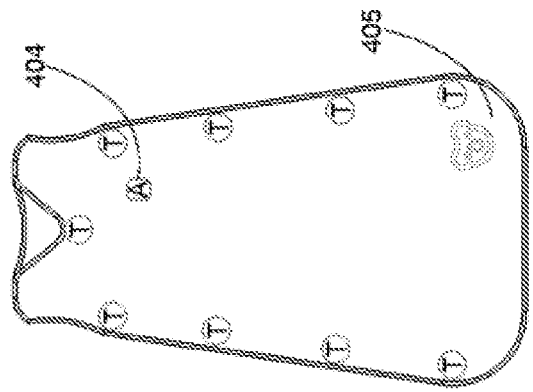
Figure 5F:
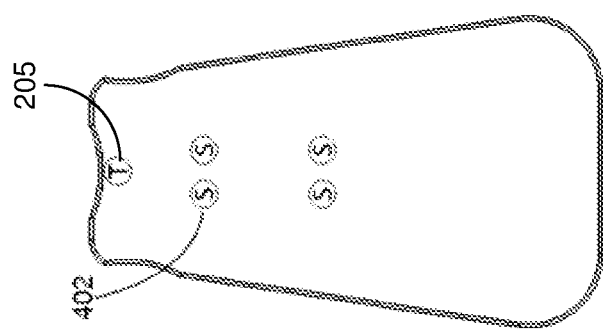
Figure 5E:
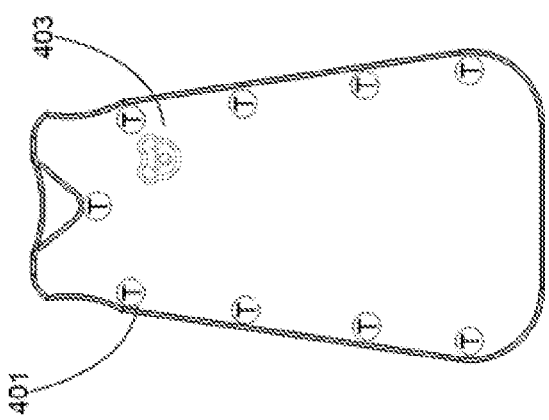

As shown in FIGS. 4A and 4B, in a third configuration, the bag 200 can include temperature sensors "T" in similar locations to the temperature sensor locations in the first and second configurations; however, in place of the accelerometer "A", the third configuration can include a plurality of strain sensors "S" located in two-dimensional (2D) patterns on the back and the front of the bag 200 to sense position/orientation, respiration and/or heart rate of the occupant. The front pattern can include 5 sensors "S" in a symmetrical "X" shape. The back pattern can include 4 sensors "S" at the corners of a rectangle. The strain sensors "S" can detect changes in pressure on their surfaces, and thus parameters as such as the heart rate, the respiration rate and the position of the occupant, as mentioned hereinbefore. The strain sensors "S" are located directly above and below a torso of the occupant of the bag 200 on the front of the bag 200 to determine the position of the occupant. If the occupant is on their stomach, the sensors "S" can be used to determine this undesirable position/posture, and the system 100 can generate and send an appropriate alert. If a strain approximately equal to the weight of the occupant is detected on the sensors on the front of the bag 200, and the sensors on the rear of the bag 200 do not detect any weight, then the system determines that the child is in an unsafe position on his/her front. As shown in FIG. 4B, the bag 200 can include one of the 2D patterns on the back of the bag 200. The strain sensors "S" on the back of the bag 200 can be used to measure the occupant's heart rate and respiration rate. As shown in FIG. 4A, in the third configuration, the processor "P", the wireless transceiver "W" and the battery "B" are located at the foot of the bag 200, similar to the second configuration. Or, as shown in FIG. 4C, the on-bag processor 102 can be located at the foot of the bag 200. In a fourth configuration (not shown), the processor "P", the wireless transceiver "W" and the battery "B" (or the on-bag processor 102) are located at the chest area, similar to the first configuration.

As shown in FIGS. 5A to 5H, fifth and sixth configurations are provided in which a 2D rectangular pattern of strain sensors "S" is added to the first and second configurations respectively. In the fifth and sixth configurations, the accelerometer "A" or the on-bag processor 102 is located at point 403, 404 above the chest of the occupant of the bag 200 in order to measure the heart rate, the respiration and the position. The strain sensors "S" are located on the rear of the bag 200 in the rectangle pattern, directly under the occupant's torso to give additional heart rate and respiration measurements. Using the accelerometer "A" in conjunction with the plurality of strain sensors "S" can improve the accuracy of the estimations of heart rate, respiration rate and position from the data processing method.

As shown in FIGS. 6A to 6C, the base station 103 can include a body 501 that contains base station electronics.

The base station electronics can include at least one camera 502, 503 in order to record video of the room, the bag 200 and/or the occupant, and/or a microphone in order to record audio of the room in which it is placed. The camera 502 and/or the microphone can be used to monitor background noise levels and/or light within the room, detect respiration, or to pick up on noises (e.g., crying) and/or movement from the occupant. The cameras 502, 503 can includes a night-vision camera (e.g., an infra-red (IR) camera) and/or a daylight camera. The night-vision camera can be a visible-and-IR camera, e.g., a digital camera without an IR filter, referred to as a "NOIR" camera. The base station electronics can include one or more base-station sensors that measure properties of the room air (ie., the environment of the base station 103), including: an on-board temperature sensor that measures the ambient air temperature within the room; a humidity sensor to measure an ambient humidity in the room; a carbon monoxide sensor to measure or detect carbon monoxide in the room; and a smoke detector to measure or detect smoke in the room. Signals and data from the camera 502, 503 microphone, and the on-board sensors can be transmitted through standard wired or wireless communication connections to the notification station 104 and/or the smart device 105.

The base station electronics can include a single-board microcomputer (e.g., a Raspberry Pi) with: a Central Processing Unit (CPU); an on-chip Graphics Processing Unit (GPU); lower level General Purpose Input Output (GPIO) pins; and on-board wireless modules (e.g., Wi-Fi 802.11n and Bluetooth) to communicate with the on-bag processor 102 (e.g., using Bluetooth) and the smart devices 105 (e.g., using Wi-Fi). The single-board computer may include a multi-camera adapter module to connect to the cameras 502, 503. The base station electronics may include an ambient light detector (e.g., an onboard photo-resistor), and the base station computer may switch the cameras 502, 503 from the daylight camera to the night-vision camera when the detected ambient light level is below a selected level, and vice versa. The base station electronics can include one or more IR lights (e.g., a plurality IR LEDs) to provide IR light, and an audio sound card adapter connected to a mini microphone as the microphone. The base station electronics can include indicators (e.g., LEDs) to indicate various states of the base station 103, including: an Idle state, Power-up state, and a Video/audio streaming state.

The body 501 of the base station 103 can include the following 3 main parts: a stand 2700, an enclosure 2400 and a cap 2500. The body 501 of the base station 103 can be manufactured by 3D printing or injection molding. The enclosure 2400 can house the base station microcomputer along with the two cameras 502, 503 and a ring of the infra-red lights surrounding the two cameras 502, 503 to provide night vision. The microcomputer and the cameras 502, 503 are mounted into place with mounting pins. The cap 2500 connects to and covers the back of the enclosure 2400, thus containing the base station electronics. The body 501 provides a pivot point 504 for the enclosure 2400 to tilt up and down, thus allowing the vertical angle of the cameras 502, 503 and microphone to be adjusted.

As shown in FIGS. 24A to 24F, the enclosure 2400 can include:

a. camera holes 2402 for the respective two cameras 502, 503 to receive light from outside the enclosure 2400;
b. recessed sections 2404 around the two holes 2402 inside the enclosure 2400 that receive camera boards (i.e., PCBs of the two cameras 502, 503);
c. a pivot mechanism for connection to the stand 2700 (e.g., pins 2406 to insert into cooperating base plate holes 2702);
d. a recessed step 2408 to receive the cap 2500;
e. large fillets and rounded edges 2410;
f. light holes 2412 around the camera holes 2402 to transmit light from the infra-red lights (e.g., light-emitting diodes); and
g. recessed areas around the light holes 2410 inside the enclosure 2400 that receive the light boards.

As shown in FIGS. 25A to 25D, the cap 2500 can include:
a. a small opening 2502 that allows a power cable (e.g., a micro-USB cable) to be connected to a power source, e.g., an available charger;
b. a stepped rim 2504 to connect to the recessed step 2408 of the enclosure 2400;
c. rounded edges 2506; and
d. space 2508 that receives the microcomputer.

As shown in FIGS. 27A to 27E, the stand 2700 can include:
a. a cooperative pivot mechanism for connection to the enclosure 2400 (e.g., the cooperating base plate holes 2702—in other implementations, the enclosure 2400 can have the holes and the stand 2700 can have the pins);
b. a charging slot 2704 for a removable portion of the on-bag processor 102 when it is removed from the bag 200—the charging slot 2704 has a cooperating second sliding mechanism that receives a first sliding mechanism of the on-bag processor 102, and power connectors (e.g., female conductive pads to receive male spring pins of the on-bag processor 102) to deliver power to charge the on-bag processor 102;
c. upright supports 2706 to hold the enclosure 2400 and allow it to pivot;
d. a base plate 2708 that is larger in footprint than the enclosure 2400 for stability; and
e. curved and soft edges 2710.

As shown in FIGS. 26A to 26D, the base station 103 can includes a microcomputer assembly with:
a. the base station microcomputer that processes the data from the on-bag processor 102; and
b. a mounting space for the base station microcomputer in the enclosure 2400, including mounting pins.

Figure 35:
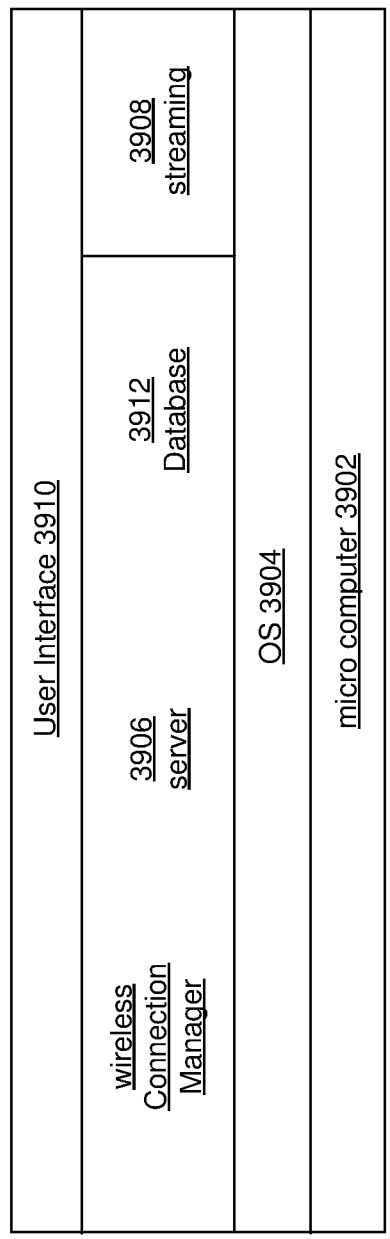
FIG. 35 is a diagram of modules in the base station microcomputer.

As shown in FIG. 35, the base station microcomputer 3902 can include the following components:
a. an operating system 3904, including an available kernel and software libraries, that provides a hardware abstraction layer, a filesystem and networking support (e.g., Linux);
b. a central webserver application 3906, which manages collection of data from the on-board processor 102 and the base station sensors (including the cameras, microphone, and on-board sensors), data storage and retrieval in a local database 3912, generation of alarms, and serving of data and alarms to the smart devices 105 and the carer notification device 104;
c. a streaming component 3908 to collect and serve the video and audio streams from the cameras 502, 503 and microphone to the smart devices 105 and the carer notification device 104;
d. a user interface 3910 that can use a web-browser to control the system 100 and change its settings and parameter values based on user inputs; and
e. a wireless connection module, e.g., Bluetooth and Wi-Fi.

As shown in FIGS. 7A to 7D, the carer notification device 104 (also known as a "carer notification unit") can include a diffused visual light indicator 601 (e.g., a glowing ball lit by an LED light). The indicator 601 can change colour and/or brightness based on the data from the on-bag processor 102 and/or the base station 103, e.g., the light can flash red if the bag's occupant is in an unsafe position, or the temperature is too high or low or the respiration has stopped, or high carbon monoxide is detected, or smoke is detected. The carer notification device 104 can notify or alert a carer of a current state/status or information from the on-bag processor 102 and/or the base station 103. The notification device 104 can include a communication receiver to receive data via standard wireless or wired communication connections (e.g., Wi-Fi). The carer notification device 104 can also include a speaker or buzzer that can provide audible alerts or pass on (i.e., stream) the sound occurring in the room from the microphone included in the base station 103. The carer notification device 104 can be used remotely from the base station 103, e.g., in a different room of a building, such as a parents' bedroom. The carer notification device 104 can be powered by an available source, e.g., a micro USB cable, connected through a port 603. The carer notification device 104 can include an interface screen 602. The carer notification device 104 can include a stand 604 with a larger footprint than the indicator 601 for stability.

The carer notification device 104 can include controller electronics, which can include: a system-on-chip (SOC) that supports wireless communications (e.g., Wi-Fi). The controller electronics communicate with the base station 103 (e.g., over Wi-Fi). The base station 103 sends alert notifications to the controller electronics of the CND 104 to perform respective actions. The SOC has a light output that can dim the indicator 601 (e.g., using a high-power channel of an LED). The indicator 601 can include coloured lights, e.g., an RGB LED, that are controlled to provide different colours based on alarm levels in the alert notifications. The buzzer can also be controlled based on alarm levels in the alert notifications.

Figure 8:
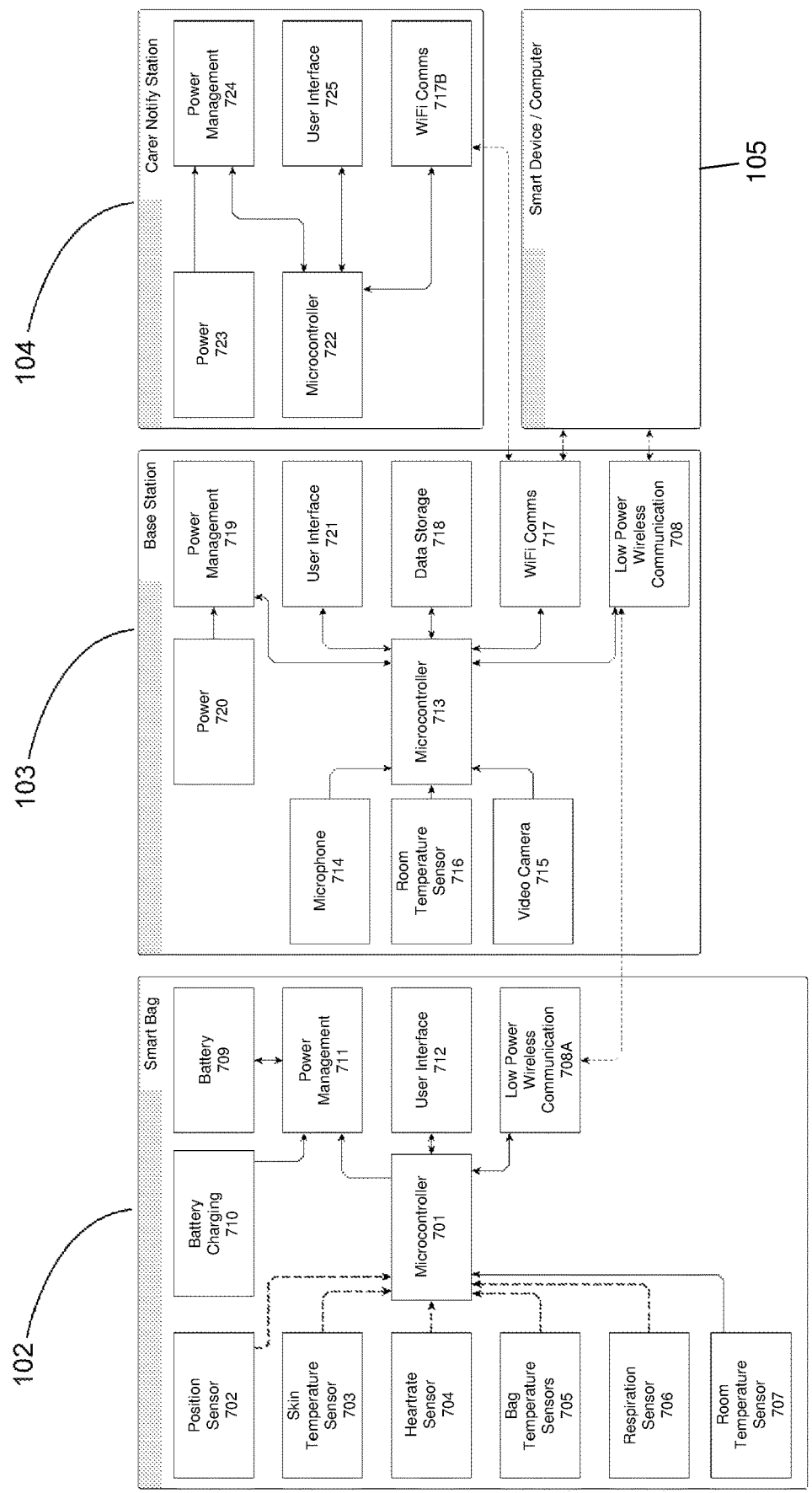
FIG. 8 is a detailed block diagram of the system.

As shown in FIG. 8, the on-bag processor 102 can include a low-power microcontroller 701, with a sleep function to conserve battery life. The microcontroller 701 receives measurement signals from the plurality of sensors 101, including those measuring position 702, skin temperature 703, heart rate 704, bag temperature 705, respiration 706 and room temperature 707. The microcontroller 701 generates measurement data from the measurement signals. The on-bag processor 102 can include a battery 709 in order to power its components. A rechargeable battery can be used within the on-bag processor 102, and battery recharging circuitry 710 can be included in the on-bag processor 102. In order to condition the power received from the battery 709, and to manage the recharging, a power management component 711 can be included in the circuitry of the on-bag processor 102. The on-bag processor 102 can include a bag user interface 712, which can include indicator lights and/or a tag control (e.g., a power button/switch). The on-bag processor 102 can include a wireless communications component 708A to report signals and data received from the microcontroller 701 to the base station 103.

As shown in FIG. 8, the base station 103 can include a wireless communications component 708B to receive the signals and data from the bag 200. This data from the bag 200 is sent to an on-board microcontroller 713 or the microcomputer of the base station 103, which collects and processes the received data. The base station 103 can include the room temperature sensor 716 in order to detect the ambient air temperature in the room. The base station 103 can include the microphone 714 and the video cameras 715 in order to record and transmit what is currently occurring in the room where the base station 103 is located. The base station 103 can include machine-readable storage 718 for storing data and instructions in order to facilitate processing in the longer-term analysis. The base station 103 can include power management circuitry 719 and a power source 720, and can be powered from a wired power connection and/or a battery. The base station 103 can include a base-station user interface 721 to provide information directly from the base station 103 to parents or carers within the room, which can include notification or status lights, buttons to connect the base station 103 to a wireless network, or a screen to display data from the sensors 101 (including data representing raw measurements, and processed data representing estimated values). The base station 103 can include a base-station wireless communications module 717A to communicate with the smart device 105 or the carer notification station 104. The wireless communications module 717A can use a higher-power protocol than the wireless communications component 708A in the bag 200, which has more limited battery power and is in closer proximity to the occupant of the bag 200.

As shown in FIG. 8, the carer notification station 104 can include a station wireless communications module 717B to communicate with the base-station wireless communications module 717A of the base station 103. The carer notification station 104 can include the on-board microcontroller 722 that processes received data from the base station 103. The carer notification station 104 can include power management circuitry 724 and a power source 723, which can be provided by a wired power connection or a battery. The carer notification station 104 can include a station user interface 725 including an indicator light and/or a speaker with which to play audio from the base station 103. The carer notification station 104 can include a screen to display the video camera output from the base station 103, or to display information, e.g., measurements from the sensors 101.

Figure 9:
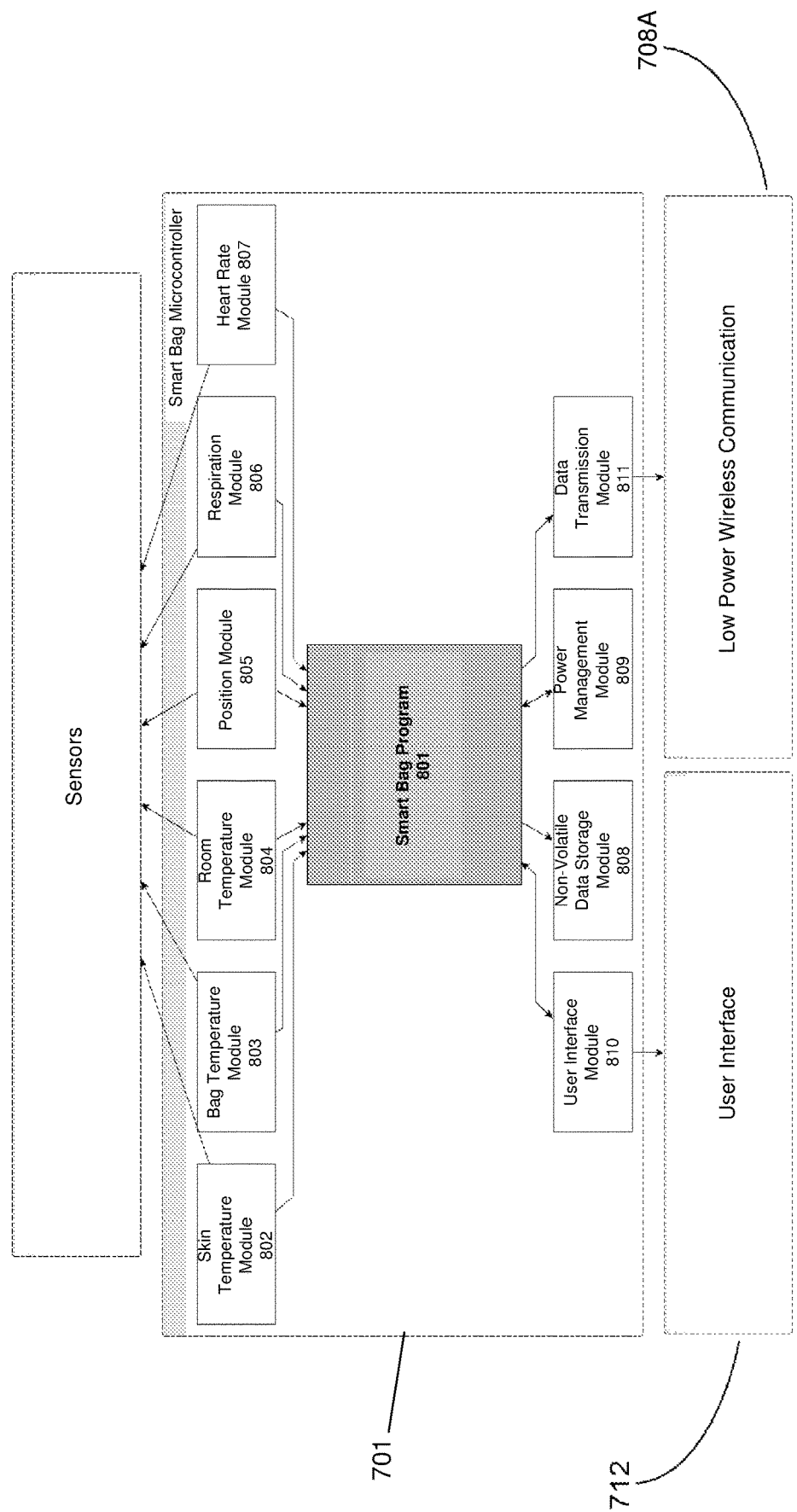
FIG. 9 is a block diagram of communicating modules in the system.

As shown in FIG. 9, the microcontroller 701 can include a plurality of communicating software and/or firmware modules. A main module 801 acts as an interface between the other modules. The measurement data from the physical sensors 101 is received and processed using the respective sensor modules: skin temperature module 802, bag air temperature module 803, room air temperature module 804, position/movement module 805, respiration module 806, and heart rate module 807. The main module 801 manages and uses non-volatile data storage 808 in order to store data for longer-term analysis. The storage 808 can be internal to the microcontroller 701 (in an EEPROM), and/or external to the microcontroller 701, including removable storage (e.g., an SD card). The microcontroller 701 can include a data transmission module 811 (e.g., Bluetooth low energy) for transmitting data to the wireless communications component 708A. The microcontroller 701 can include a power management module 809 to execute recharging detection or automatic sleep modes. The microcontroller 701 can include a user-interface module 810 which controls and receives commands from the user interface 712.

The microcontroller 701 can initialise peripherals of the microcontroller 701, establish and maintain the wireless connection (e.g., Bluetooth), and collect and process the measurement signals.

Figure 34:
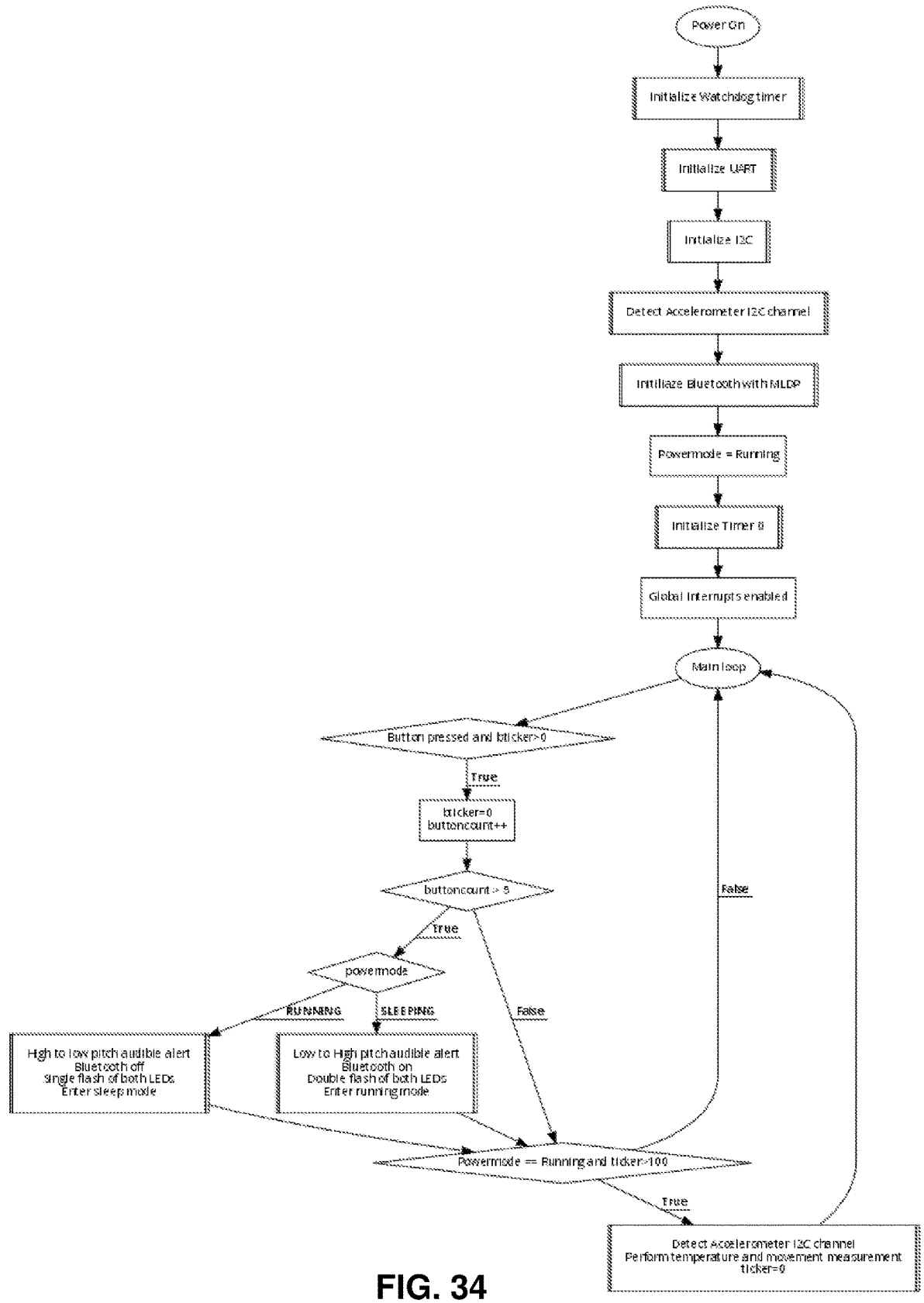
FIG. 34 is a flow diagram of operation of the tag.

As shown in FIG. 34, the microcontroller 701 performs the following method steps:

a. upon being powered up, configure the watchdog timer, UART, and I2C peripherals;

b. configure the transmission module 811 (Bluetooth) via the UART, including (i) setting the device identifier as a Smart Bag, and (ii) commanding the transmission module 811 to begin advertising this identifier—the transmission module 811 is now ready to accept a connection request from the base station 103;

c. configure a hardware timer to create an interrupt at a selected interval (e.g., 1 millisecond);

d. set a power mode flag to indicate that the on-bag processor 102 is in running mode rather than energy-saving mode;

e. globally enable hardware interrupts before entering a main loop;

f. in the main loop, check the state of the tag control (e.g., the power button or switch);

g. if the tag control has been activated (e.g., pressed) for longer than a selected duration (e.g., 0.5 seconds), switch the power mode from the running mode to the energy-saving mode (or vice versa);

h. if the power mode is changed to the sleeping mode, then: generate an audible alert comprising of a high pitch tone followed by a low pitch tone; power down the transmission module 811; generate a single flash of both lights ("LED" on the main tag PCB 2302 see FIG. 22); and set a power mode flag to indicate the sleeping mode;

i. if the power mode is changed to running mode, then: generate an audible alert comprising of a low pitch tone followed by a high pitch tone; generate two flashes from both lights ("LED"); and set the power mode flag to the running mode;

j. if the power mode flag is in the running mode, and a selected polling delay (e.g., 100 milliseconds) has passed, then perform a sensor data collection routine, including: query the sensors 101 for their measurements to generate respective results as the measurement signals; and transmit the results as the measurement data via the transmission module 811 if the connection to the base station 103 is active; and k. repeat the main loop.

Figure 10:
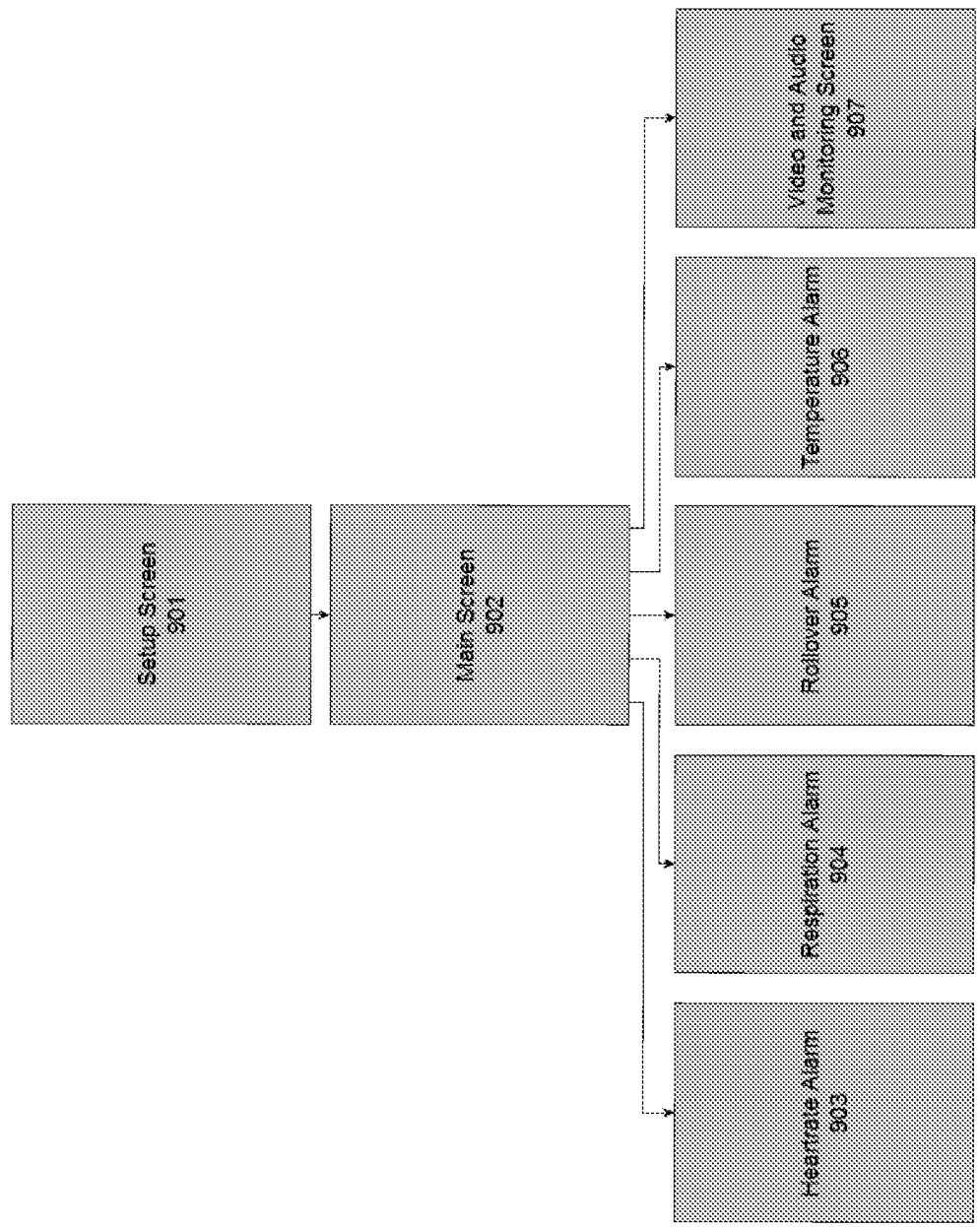
FIG. 10 is a state diagram of a user interface of the system.
Figure 15B:
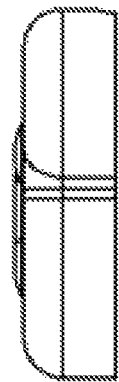
FIGS. 15A-15E are diagrams of a tag front of a tag of the system.
Figure 15E:
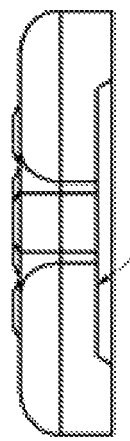
Figure 15C:
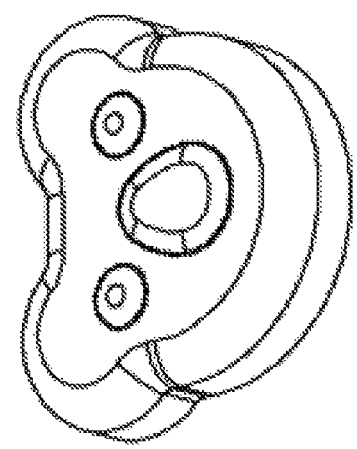
Figure 15A:
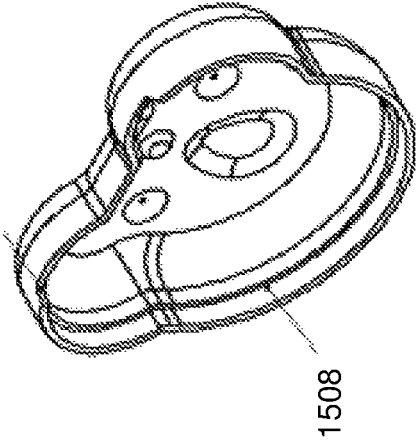
Figure 15D:
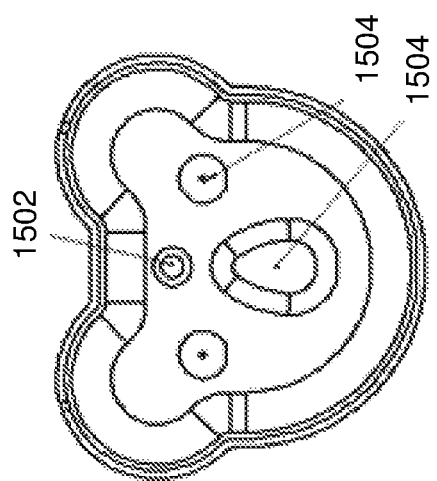
Figure 20A:
FIGS. 20A-20E are assembly diagrams of the tag.
Figure 20B:
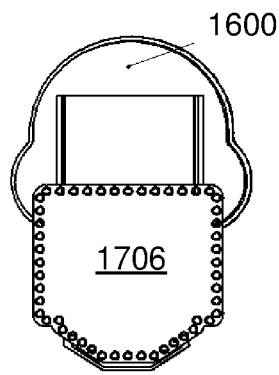
Figure 20C:
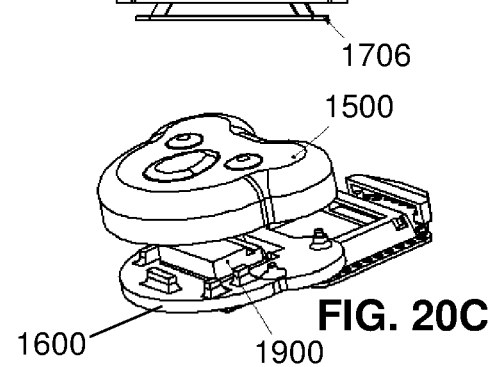
Figure 20D:
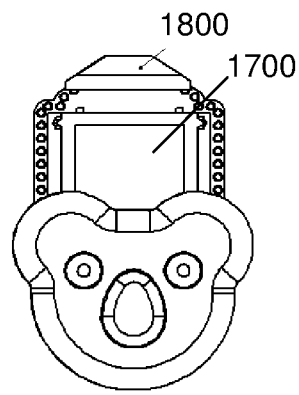
Figure 20E:
Figure 21A:
FIGS. 21A-21D are assembly diagrams of the tag back and the tag slot.
Figure 21B:
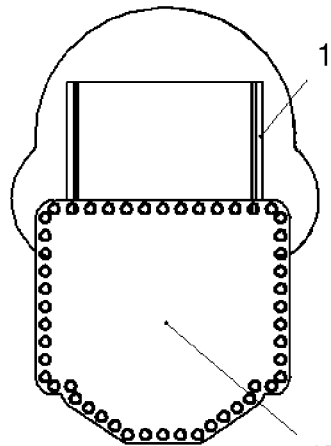
Figure 21C:
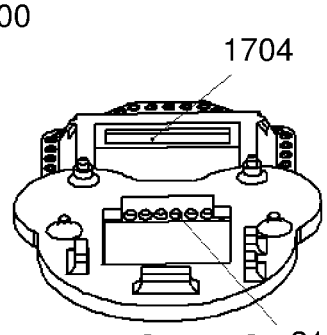
Figure 21D:
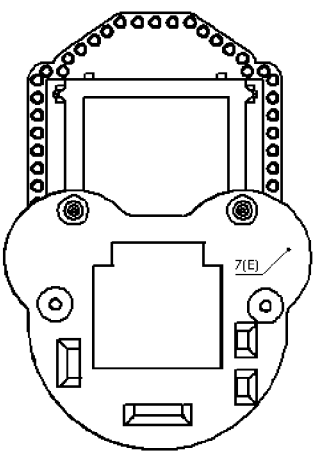

The application in the smart device 105 receives, processes and displays data based on data transmitted from the base station 103. As shown in FIG. 10, a state machine of the user interface (UI) of the application can include an initial state corresponding to an initial setup screen 901 which displays logos, a welcome message and any relevant instructions required to pair the application with the correct base station 103. Once pairing with the base station 103 or the bag 200 (via the respective wireless communication modules) is completed successfully, the user is presented with a monitoring screen in a monitoring state: the monitoring screen shows the current statuses of the sensors 101 and base station 104. In circumstances when the data being received is abnormal or beyond previously defined limits, a number of alarm screens are available in respective alarm states. A heart rate alarm screen 903 can alert if the heart rate is too high or too low. A respiration alarm screen 904 can alert if the respiration of the occupant is too fast or slow. A rollover alarm screen 905 can alert if the occupant of the bag 200 has rolled onto their front or side. A temperature alarm screen 906 can trigger if the temperature in the bag 200, room or skin is too high or low. The state machine of the user interface (UI) can include a video/audio state that provides a monitoring screen 907 that display outputs of the video and/or audio sensors on the base station 103, allowing parents to view and/or listen to what is happening in their child's room from wherever they are within the house (i.e., remotely) without disturbing the child.

As shown in FIGS. 11A and 11B, the bag 200 can include integrated cooling vents 1001 in the fabric of the bag 200. The vents 1001 allow carers to respond to an alert that the temperature is too high. The vents 1001 are adjustable to control air flow between an interior of the bag 200 and the surrounding environment. The vents can include mesh. The vents are integrated into the bag 200. The vents can be referred to as cooling vents. The vents can be closed by a flap (now shown) in the bag fabric, e.g., the insulated wall of the bag 200. The vents 1001 provide a gap in the insulation between the occupant and the surrounding environment. This gap in the insulation allows the parent or carer to reduce the ambient temperature within the bag 200 in response to a high temperature alert by opening the vents, or to increase the ambient temperature within the bag 200 by closing the vents. For ease of use, the vent flaps can be fastened closed using respective zips, press studs, clasps or hook-and-loop tape. As shown in FIG. 11A, the vents 1001 can include a central front vent on the front of the bag 200 (this vent can have a central front flap). As shown in FIG. 11B, the vents 1001 can include a plurality of side-back vents, located between the centre and the respective side seams of the back, located to allow some air flow even when the centre of the back is pressed into a supporting bed or mattress (these back vents can have respective back side flaps).

As shown in FIG. 12, the bag 200 can include four layers: inner fabric layer 1101, insulation layer 1103, outer fabric layer 1104, and a loom 1102 (which can be referred to as a "circuitry layer", "cable harness", "wire harness", "cable assembly", "wiring assembly" or "wiring loom"). The loom 1102 can include the sensors 101 and at least portions of the wiring. The loom 1102 is located and attached (stitched into one of the other layers) between the inner layer of fabric 1101 and the insulation layer 1103 in order to isolate them from damage from the occupant while still keeping them in close enough proximity to gather accurate results, thus potentially increasing the durability of the system and reducing damage caused by washing the bag 200, by securing the sensors and wiring. This can have the added benefit of comfort for the occupant of the bag 200 as they are not in direct contact with any wires or sensors.

As shown in FIG. 13A, the conductive connections in the bag 200 can be provided by wires 1201, with copper strands surrounded by insulation, that are stitched into the bag fabric 1202 in order to prevent movement and to increase durability. Copper wire provides low attenuation through the conductive connections. As shown in FIG. 13B, the conductive connections in the bag 200 can be provided by electrically conductive fabrics 1203 in order to integrate the wiring of the sensors 101 directly into or onto a fabric layer of the bag 200. The conductive fabrics 1203 offer a very high level of flexibility and durability, which can assist with product longevity, especially when taking into account the mechanical stresses the conductors will undergo while being washed.

As shown in FIGS. 14A and 14B, in a singlet configuration, a singlet 1304 is integrated into a sleeping bag 1301, which in other respects can include the features of the bag 200. This configuration is designed to decrease unwanted movement signals from the chest of the occupant of the bag 1301 to an accelerometer 1305. Due to movement of the occupant or the bag 200, there can be a significant amount of noise generated and passed onto the accelerometer "A". Through ensuring that the accelerometer 1305 is closely linked to the chest movement, this singlet configuration may significantly reduce the noise measured. In this configuration, the bag 1301 has an opening zip or clasp 1303 that allows easy access for the occupant into the bag 1301.

As shown in FIGS. 15A to 21D, the on-bag processor 102 (which is also referred to as the "tag") can include tag electronics and a tag enclosure with the following individual components: a tag back 1600, a tag front 1500, a tag slot 1700, a slot cover 1800, and a step block 1900. In an assembly process, the tag front 1500 and the tag back 1600 are assembled together, with the step block 1900 placed inside, to form the removable portion of the on-bag processor 102. The removable portion is referred to as an "assembled tag". This assembled tag is reversibly attached to the tag slot 1700 by sliding the assembled tag along tracks of the tag slot 1700, and locking the assembled tag with locking lugs. Thus the tag slot 1700 is a tag receiver. The slot cover 1800 covers conductive contact connectors (in the form of female conductive pads 3602, e.g., pogo pins), and a bag interconnecting PCB 2304 onto which the conductive contact connectors are soldered. The step block 1900 is mounted in a cavity in the tag back 1600 to hold cooperative conductive contact connectors (i.e., that connect to the conductive contact connectors, in the form of male spring-loaded pins, e.g., pogo pins) in place. The male spring-loaded pins are soldered to an inner tag PCB 2306, which is soldered to the main tag PCB 2302, thus the male spring-loaded pins project in the insertion direction of the assembled tag, i.e., in the plane of the main tag PCB 2302. The tag slot 1700 is sewn onto the bag 200, and the sensor conductive connections (e.g., the wires 1201 or the electrically conductive fabrics 1203) extend from the back side (i.e., the opposite side from the tag front 1500) of the tag slot 1700, and extend into and around the bag 200. The tag enclosure can be produced by different manufacturing methods, including 3D printing (e.g., using ABS plastic) and injection molding. Components of the on-bag processor 102 that are not in the removable portion, and that remain attached to the bag 200 (i.e., including the tag slot 1700, the slot cover 1700, the bag interconnect PCB 2404, the terminated conductive connections and the conductive contact connectors (in the form of female conductive pads 3602, e.g., pogo pins) are collectively referred to as an "attached portion" of the on-bag processor 102.

Figure 23A:
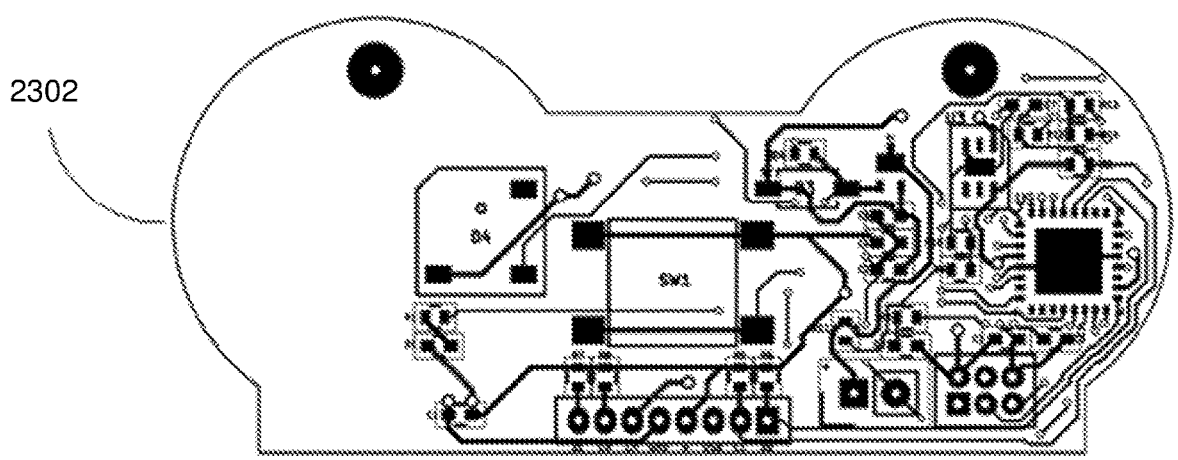
FIGS. 23A-23D are diagrams of a printed circuit board of the tag.
Figure 23B:
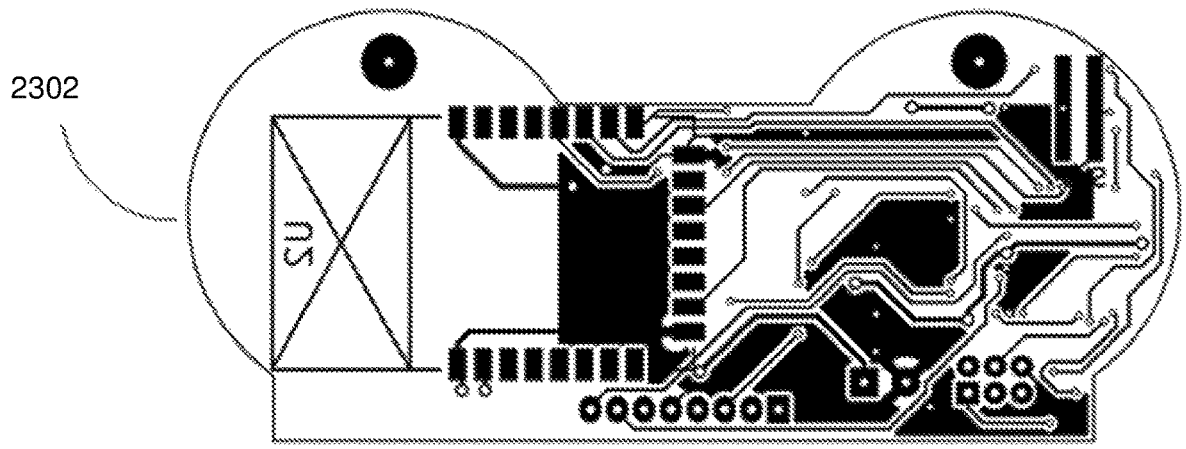
Figure 23C:
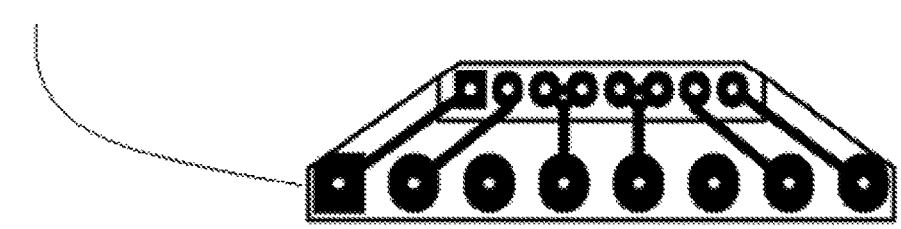
Figure 23D:
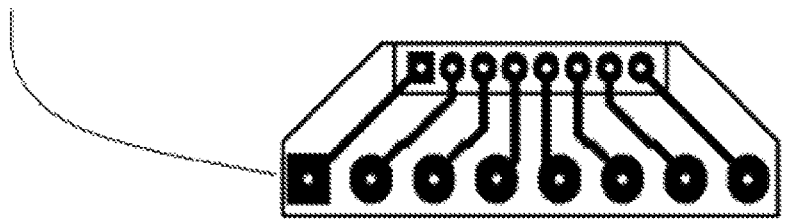
Figure 24A:
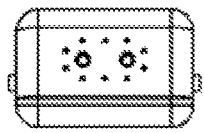
FIGS. 24A-24F are diagrams of an enclosure of the base station.
Figure 24B:
Figure 24C:
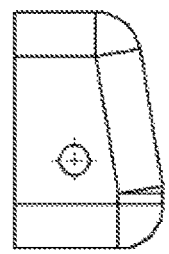
Figure 24D:
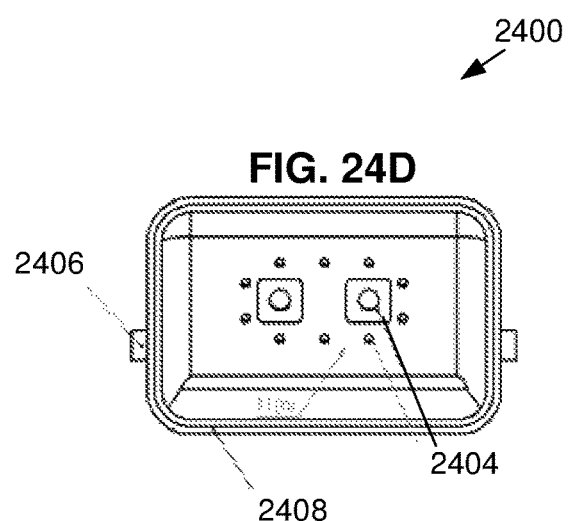
Figure 24E:
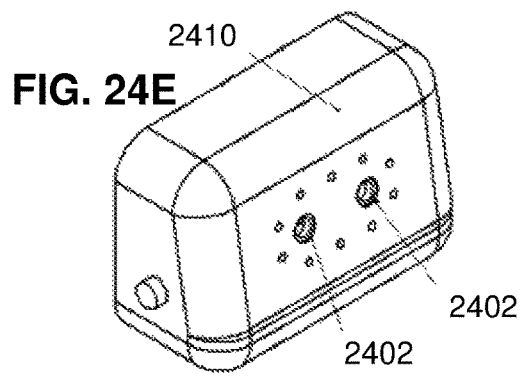
Figure 24F:
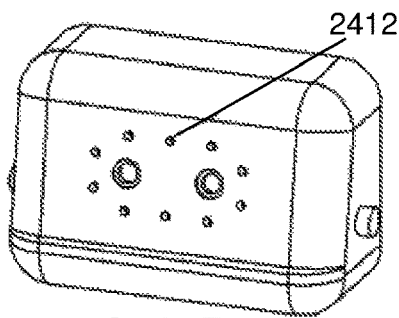
Figure 25A:
FIGS. 25A-25D are diagrams of a cap of the base station.
Figure 25B:
Figure 25C:
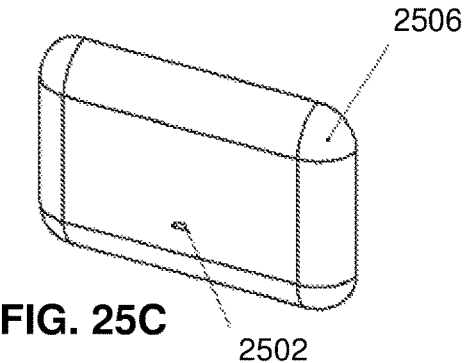
Figure 25D:
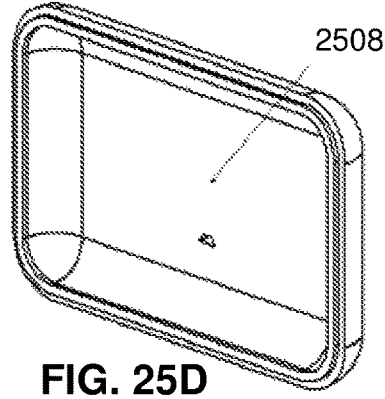
Figure 26A:
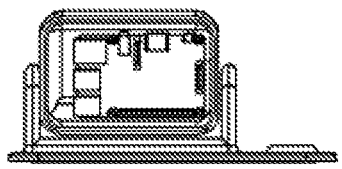
FIGS. 26A-26D are assembly diagrams of the base station and its microcomputer.
Figure 26B:
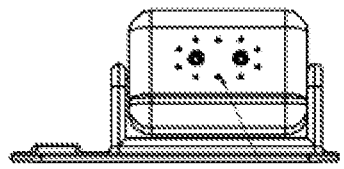
Figure 26C:
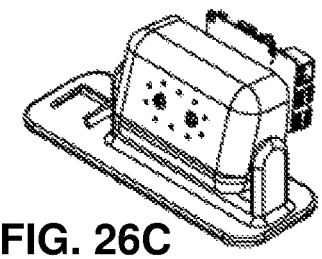
Figure 26D:
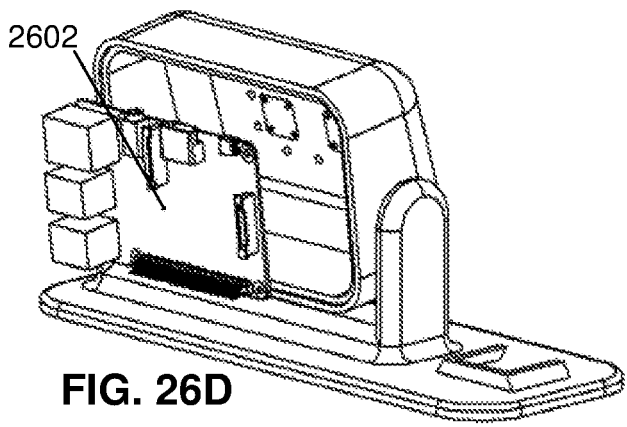
Figure 27A:
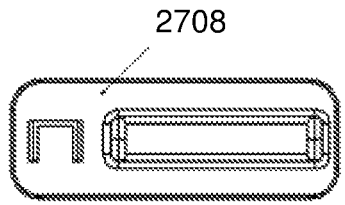
FIGS. 27A-27E are diagrams of a stand of the base station.
Figure 27B:
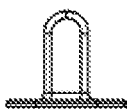
Figure 27C:
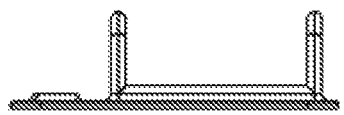
Figure 27D:
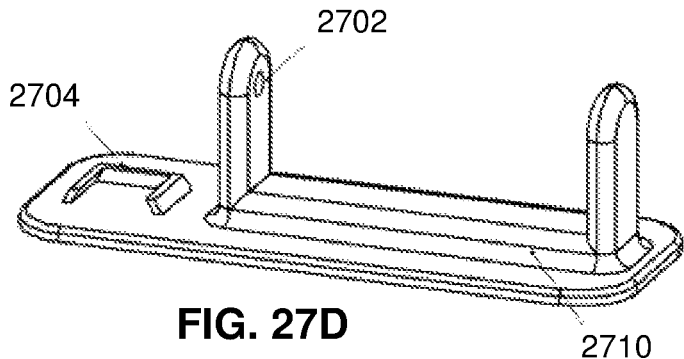
Figure 27E:
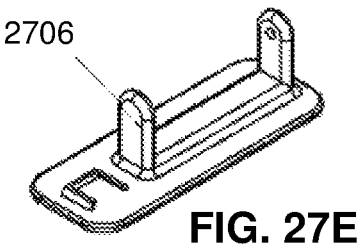

As shown in FIGS. 15A to 15E, the tag front 1500 can include:

a. an internal projection 1502 that reaches the tag control (e.g., the switch) on the main tag PCB 2302 ("SW1", see FIG. 23A) when in the assembled tag, thus allowing activation of this tag control by applying manual pressure to the front side (i.e., the side away from the tag back 1600) of the tag front 1500;

b. decorations 1504 (e.g., eyes and nose) that project a uniform distance from the front face for uniform top thickness;

c. a cut-out 1506 in the top-side wall (i.e., the side facing in the direction which the assembled tag is slid towards the tag slot 1700) to allow a portion of the tag slot 1700 to pass through to connect the assembled tag; and d. a step 1508 from the rim of the side walls to fit over a cooperating step of the tag back 1600 in the assembled tag.

As shown in FIGS. 16A to 16E, the tag back 1600 can include:
a. resilient locking nodes 1602 on opposite sides of a slot for reversibly locking with respective resilient locking lugs 1712 of the tag slot 1700, thus allowing the tag back 1600 to be manually locked to the tag slot 1700, and manually removed from the tag slot 1700;
b. fillets 1604 on opposite sides of the slot, above the locking nodes 1602, allowing easier fit of the tag back 1600 when it is slid onto the tag slot 1700;
c. battery mounting lugs 1606 that mount the battery 709 in the assembled tag;
d. PCB mounting lugs 1608 that mount the main tag PCB 2302 in the assembled tag;
e. first tracks 1610 on the sides of a first sliding mechanism 1616 that slide along cooperating second tracks of the tag slot 1700;
f. connector holes 1612 shaped to receive the cooperative conductive contact connectors (in the form of the male spring-loaded pins) from the main tag PCB 2302;
g. a cable slot 1614 to allow a battery cable to extend from the main tag PCB 2302; and
h. the first sliding mechanism 1616 that slides into or onto the cooperating second sliding mechanism of the tag slot 1700 to removably hold the tag back 1600.

As shown in FIGS. 17A to 17D and 36A to 36D, the tag slot 1700 can include:
a. a plurality of resilient cover lugs 1702 (also referred to as "locking pins") that engage with respective recessed sections 1804 of the slot cover 1800 to attach the slot cover 1800 to the tag slot 1600;
b. a connector slot 1704 that receives the conductive contact connectors (in the form of the female conductive pads 3602) that project from the bag interconnecting PCB 2304 to connect by touching the cooperative conductive contact connectors (in the form of the male spring-loaded pins) from the main tag PCB 2302 when the assembled tag is slid into the tag slot 1700;
c. a base plate 1706 that attaches to the bag 200 by sewing;
d. sewing holes 1708 that receive thread to attach the tag slot 1600 to the bag 200;
e. a plurality of angled sides 1710 of the cooperating second sliding mechanism;
f. the filleted locking lugs 1712 to allow for easy locking with the locking nodes 1602 of the tag back 1600; and
g. a recessed slot 1714 between the sewing holes 1708 along an entry aperture to the cooperating second sliding mechanism (i.e., between the angled sides 1710) to allow the thread to sit flush, thus not interfere with the first sliding mechanism sliding into/onto the cooperating second sliding mechanism.

In some implementations, the first sliding mechanism is a male projection, and the cooperating second sliding mechanism is a female receiving slot. In other implementations, the first sliding mechanism is a female receiving slot, and the cooperating second sliding mechanism is a male projection.

As shown in FIGS. 18A to 18D, the slot cover 1800 can include:
a. conductor holes 1802 to allow the conductive connections to extend from the tag electronics (specifically from the inner tag PCB 2306) to the sensors; and
b. the recessed sections 1804 to receive the respective cover lugs 1702 of the tag slot 1700.

As shown in FIGS. 19A to 19C, the step block 1900 can include:
a. a cut out area 1902 that receives undersides of soldered pins that extend from the main tag PCB 2302, i.e., receives an underside of the soldered pins connecting from the main tag PCB 2302 to the inner tag PCB 2306; and
b. a raised area with a selected height to lock in the cooperative conductive contact connectors (in the form of the male spring-loaded pins) of the main tag PCB 2302.

As shown in FIGS. 20A to 20E and 36A to 36D, in the on-bag processor 102 (or "tag") in its fully assembled condition:
a. the slot cover 1800 attaches to the back of the tag slot 1700 with the locking lugs 1702 fitting into the recessed sections 1804, and the slot cover 1800 covers the bag interconnections PCB 2304 and the terminated conductive connections;
b. the tag front 1500 is placed on top of the tag back 1600;
c. the step block 1900 is placed into a recess in the tag back 1600 to secure in place the cooperative conductive contact connectors (in the form of the male spring-loaded pins) of the main tag PCB 2302, and
d. the base plate 1706 is sewn to the bag 200 so that the on-bag processor 102 is nearly flush with the outer surface of the bag material.

As shown in FIGS. 21A to 21D and 36A to 36D, the tag back 1600 and the tag slot 1700 connect as follows:
a. the tag slot 1700 slides onto the tag back 1600 and locks into place with the locking lugs 1702;
b. the cooperative conductive contact connectors 2105 (in the form of the male spring-loaded pins) of the main tag PCB 2302 fit through the connector holes 1612, thus allowing them to connect to the conductive contact connectors (in the form of the female conductive pads 3602) that project from the bag interconnecting PCB 2304; and
c. the tag back 1600 slides along the tracks of the cooperating second sliding mechanism of the tag slot 1700 until the cooperative conductive contact connectors 2105 are adjacent the connector slot 1704 that receives the conductive contact connectors (in the form of the female conductive pads 3602).

Figure 22:
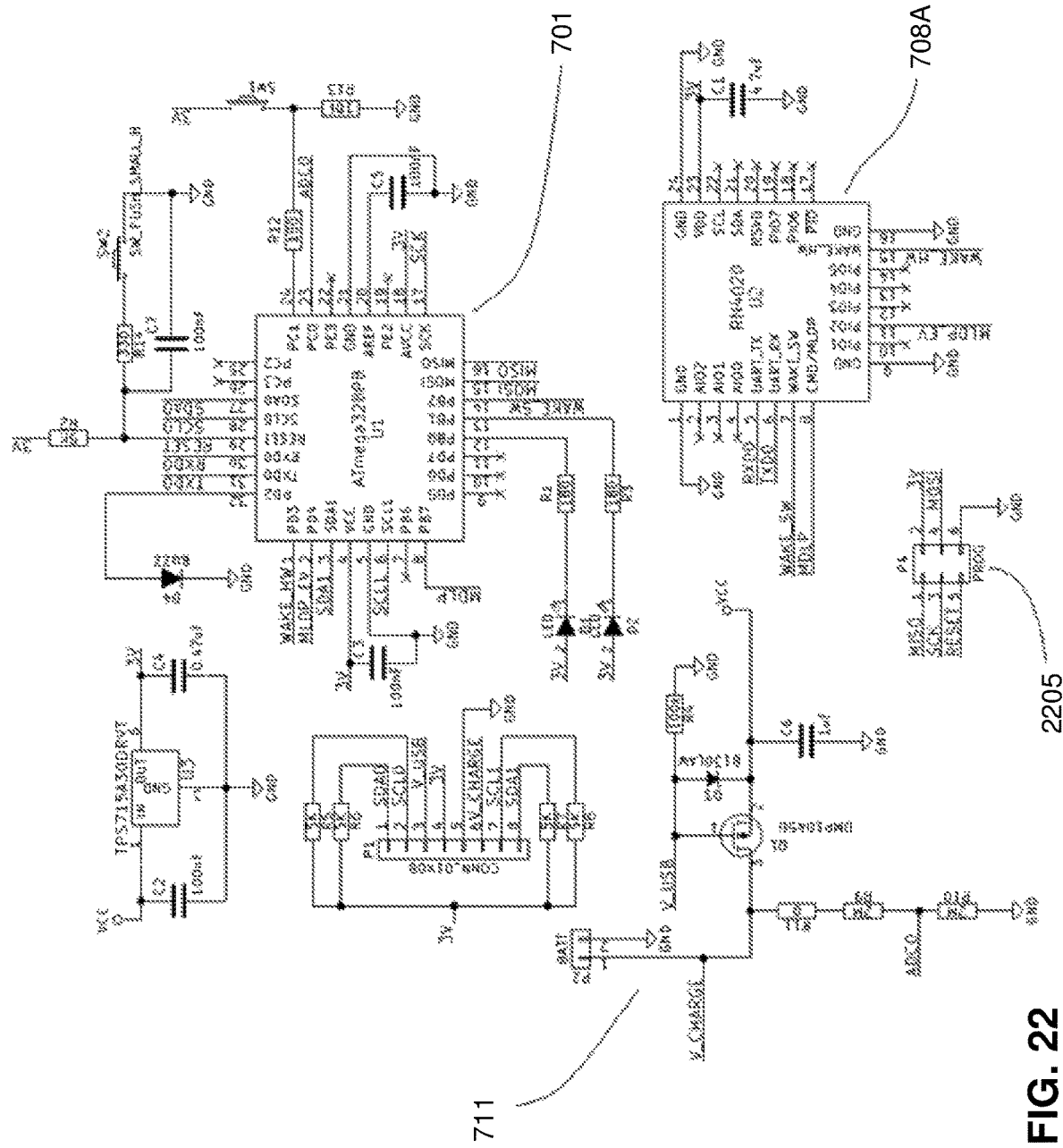
FIG. 22 is a diagram of an electronic circuit of the tag.

The conductive pads 3602 provide reversible electrical connections between the assembled tag and the sensors 101 while still providing a generally smooth surface, i.e., without plug pins or plug sockets, making the exposed surfaces of the attached portion of the on-board processor 102 easier to keep clean and dry. As shown in FIG. 22, the tag electronics can include:
a. one or more signal inputs in the form of electronic bus lines that connect to the conductive connections to receive signals from the sensors 101 (using an available interface bus protocol);
b. the wireless communications component 708A (module) configured to communicate with the base station 103 according to an available protocol that operates at low power (e.g., Bluetooth low energy);
c. the battery 709 in the form of a small-capacity battery as used in wearable technologies (e.g., Li—Po);
d. the power management component 711 including a charging circuit configured for load sharing, i.e., to allow the tag on-bag processor 102 to still communicate with the base station 103 whilst charging the battery 709;

e. the microcontroller 701 with embedded routines that read the sensor signals to gather the signal data, optionally transform the signal data (e.g., translate the data representing the measurement signals from binary data to a readable format, and convert it to degrees Celsius, and aggregate the data from all of the sensors 101 to minimize transmission time), and transmit the transformed data over the wireless connection—the microcontroller 701 can be configured to low power operation to improve running time of the on-bag processor 102, and f. a programming breakout circuit 2205.

As shown in FIGS. 23A to 23D, the tag electronics include:

a. the main tag PCB 2302;
b. the bag interconnect PCB 2304; and
c. the inner tag PCB 2306.

The PCBs are fabricated through available PCB fabrication processes.

As shown in FIG. 28, the loom 1102 can include:

a. a tab slot assembly 2802;
b. the conductive connections 2804 (e.g., the wires 1201 or the electrically conductive fabrics 1203), e.g., 4-core, insulated loom connecting wire, between the sensors 101, therefore one piece of the conductors per sensor (e.g., 9), and one corresponding piece of heat shrink cover for each piece of the conductors;
c. one or more (e.g., two sets of 4) temperature sensor assemblies 2806 connected to the sensor conductors; and
d. at least one accelerometer sensor assembly 2808 connected to the sensor conductors.

The tab slot assembly 2802 includes the bag interconnecting PCB 2304 with the conductive contact connectors (in the form of the female conductive pads 3602) exposed, covered by a tab slot cover. The loom 1102 can have four temperature sensors on each of two bus lines (i.e., serial lines) formed by the conductive connections 2804. The tab slot assembly 2802 can be constructed using a tab slot, the tab slot cover, the conductive contact connectors (female), and the bag interconnecting PCB 2304. The conductive contact connectors and the bag interconnecting PCB 2304 are soldered together, and then soldered to two lengths of the conductive connections 2804 to form an initial portion of the two bus lines. The assembled conductive contact connectors, bag interconnecting PCB 2304 and initial bus lines are placed into the tab slot, which is filled with insulated potting (e.g., epoxy resin) then covered by the tab slot cover. The bus lines are terminated to the temperature sensor assemblies 2806 and/or the accelerometer sensor assembly 2808.

As shown in FIGS. 29A and 29B, each temperature sensor assembly 2806 includes:

a. the terminating piece 2902 of the conductive connections;
b. insulated connecting wire 2904 from the terminating piece 2902 to the temperature sensor PCB 2910;
c. an outer layer 2906 of the heat shrink cover over the conductive connections and the temperature sensor PCB 2910;
d. insulated potting 2908 (e.g., epoxy resin) covering the conductive connections and the temperature sensor PCB 2910 for strength and waterproofing; and
e. the temperature sensor PCB 2910 mounted in the loom 1102.

The temperature sensor PCB 2910 includes a thermally conductive extension to aid in accurate temperature determination. The extension goes beyond (i.e., protrudes from) the waterproofing layer(s) of the insulated potting 2908 and the outer layer 2906, and into the surrounding air, in order to increase the accuracy of the temperature reading. The extension is highly thermally conductive and allows for the surrounding ambient air temperature of the inside of the bag 200 to be passed through to the temperature sensor. The extension includes thermal conductive material, e.g., copper from the PCB process, that extends to one or the conductive projections of the temperature sensor, e.g., a pin of a sensor chip (e.g., the ground pin). Thus the extension is electrically conductive and thermally conductive, and is connected to the temperature sensor both thermally and electrically.

The accelerometer sensor assembly 2808 can be located in the 5th position away from the tab slot assembly.

In instances where the conductive connections include the conductive fabrics 1203, it can include four track conductive fabric strips 3002.

As shown in FIG. 30A, in some instances the conductive fabric strips 3002 can be terminated by stitching from the connected sensor 3004 to the conductive fabric strips 3002 with conductive thread 3006 (e.g., stainless steel) that is soldered to the PCB and covered in epoxy 3008 to insulate and secure the conductors. The conductive fabric strips 3002 can also be sealed with epoxy 3010 to aid with waterproofing.

As shown in FIG. 30B, in some instances the conductive fabric strips 3002 can be terminated by stitching from the conductive fabric strips 3002 to female micro metallic buttons 3012 using the conductive thread 3006 (e.g., stainless steel). The male micro metallic buttons 2012 are soldered to the PCB and plugged into the female button sockets. The buttons 3012 are then glued with epoxy.

Figure 31:
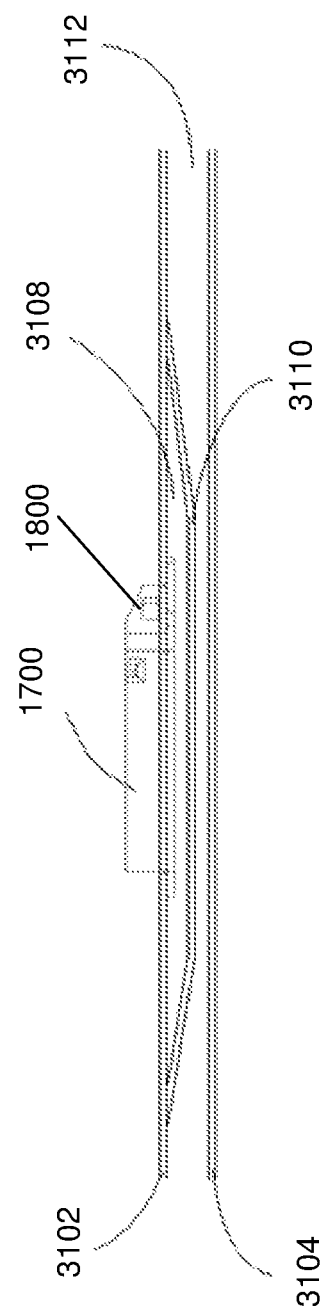
FIG. 31 is side-view diagram of material layers of the sleeping bag.
Figure 33:
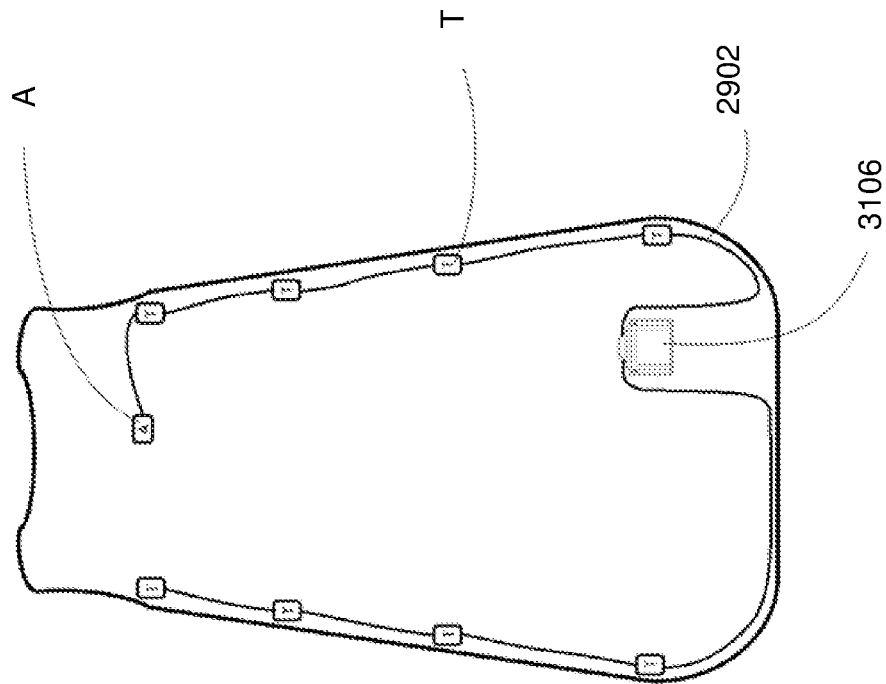
FIG. 33 is an internal front view of the sleeping bag showing the loom assembly connected to the tab slot.
Figure 32:
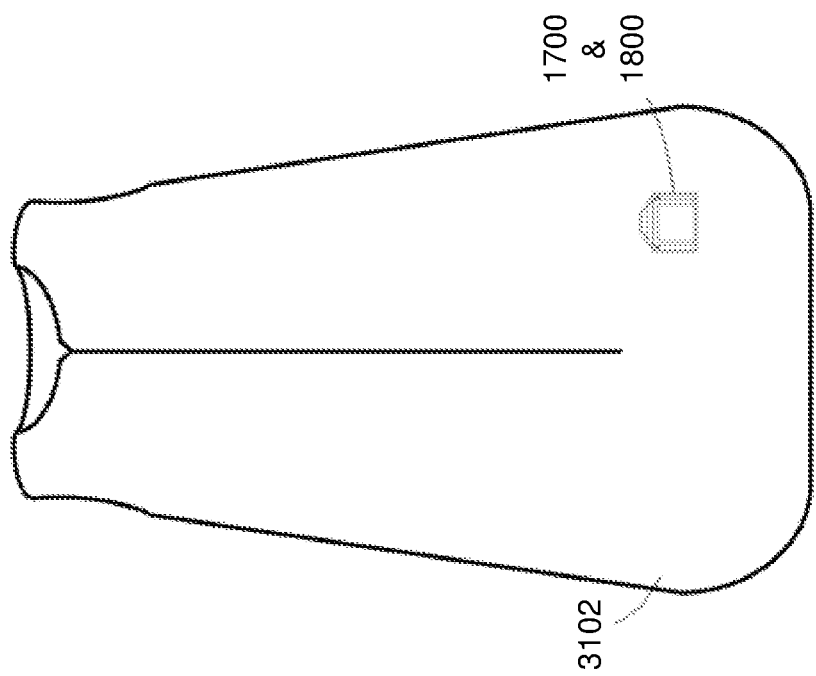
FIG. 32 is a front view of the sleeping bag with the tab slot.

As partially shown in FIGS. 31 to 33, the bag 200 can include:

a. an outer material layer 3102;
b. an inner material layer 3104;
c. the tag slot 1700 with the slot cover 1800;
d. an outer layer of batting 3108;
e. a canvas strengthening layer 3110;
f. an inner layer of batting 3112;
g. the accelerometer "A";
h. the temperature sensors "T"; and
i. the sensor conductors 2902.

The bag 200 can include 4 layers of materials: the 2 layers of batting, the 1 material outer layer, and the 1 inner layer of material. The layers of batting can have a mutually equal thickness. A fifth layer of the canvas material can be added to a section later. The outer layer of batting 3108 is secured to the outer material layer 3102 via a plurality of rows (e.g., 6 rows) of straight stitches. The inner layer of batting 3112 and the inner layer of material 3104 are also fastened together via a plurality of rows (e.g., 6 rows) of straight stitches. The loom 1102 and the sensors 101 are distributed and located between the inner layer of material 3104 and the inner batting layer 3112, along the side seams. The sensors 101 are secured to the inner material layer 3104 by stay stitches. The sensors 101 are further stitched onto the inner layer of batting 3112. The conductive connections are secured by stay stiches alongside the seam to prevent movement and add durability. The canvas material 3110 is sewn into the bag 200 where the on-bag processor 102 is to be attached. The canvas material 3110 is located between the two layers of batting 3108, 3112. The base plate 1706 is stitched to the canvas layer 3110 through the sewing holes 1708. The outer layer 3102 is then opened to allow the tag slot 1700 through. The base plate 1706 is then secondly stitched to the outer layer 3102 through the sewing holes 1708. The side seams are finished with an over-locking style blanket stitch. The back and front are then fastened together with a straight stitch. A seam allowance (e.g., 1 cm) is used to prevent fraying and increase durability. Bias binding is used on the length of the inner side seam of the bag 200 to provide mechanical protection to the sensors and inner stitching, which further safeguards the seams The outer material layer 3102 and the inner material layer 3104 can be breathable fabric, e.g., woven cotton, linen, synthetic polymer and/or silk.

Many modifications will be apparent to those skilled in the art without departing from the scope of the present invention as hereinbefore described with reference to the accompanying drawings.

The invention claimed is:

1. A sleeping bag system, including:
    a sleeping bag that is washable with water, including in a laundry machine, wherein the sleeping bag includes a monitoring system that includes:
    a plurality of sensors, including:
        at least one temperature sensor implanted into or onto fabric of the sleeping bag configured to measure an internal air temperature in the sleeping bag and/or a skin temperature of an occupant in the sleeping bag, and
        a movement sensor implanted into or onto the fabric the sleeping bag to measure movement of the sleeping bag, wherein the movement sensor includes a plurality of strain sensors located in a first two-dimensional (2D) pattern on the front of the bag and a second 2D pattern on the back of the bag;
    electronic circuitry for the sensors located in the sleeping bag; and
    an enclosure that is removably attachable to the bag, the enclosure including:
    an on-bag processor,
    a wireless transceiver to communicate information represented by measurement data from sensor signals representing the measurements from the sensor, and
    a battery for powering the monitoring system.

2. The sleeping bag system of claim 1, wherein the movement sensor includes an accelerometer.

3. The sleeping bag system of claim 1, wherein the plurality of sensors includes a heart-rate sensor located in the sleeping bag configured to monitor a heart rate of an occupant, wherein the heart-rate sensor includes at least a portion of the plurality of strain sensors.

4. The sleeping bag system of claim 1, wherein the plurality of sensors includes a respiration-rate sensor located in or on the sleeping bag configured to monitor a respiration rate of an occupant, wherein the respiration-rate sensor includes at least a portion of the plurality of strain sensors.

5. The sleeping bag system of claim 1, wherein the plurality of sensors includes a room-temperature sensor located on the sleeping bag to measure an ambient room temperature of a surrounding environment.

6. The sleeping bag system of claim 1, wherein the plurality of sensors includes a bag-orientation sensor located in or on the sleeping bag to measure an orientation of the sleeping bag, wherein the bag-orientation sensor includes an accelerometer and/or a combination of the strain sensors.

7. The sleeping bag system of claim 1, wherein the electronic circuitry includes conductive textiles and/or insulated wire.

8. The sleeping bag system of claim 1, including a base station that communicates electronically with the sleeping bag, and processes data from the sensors.

9. The sleeping bag system of claim 8, configured to generate one or more alerts for care when:
    the system determines that the skin temperature of the occupant is too high or low based on a comparison to one or more predetermined skin-temperature levels;
    the system determines that the internal temperature of the sleeping bag is too high or low based on a comparison to one or more predetermined bag-temperature levels; and/or
    the system determines that the occupant is in an unsafe position based on processing data representing the movement measurements.

10. The sleeping bag system of claim 9, wherein the on-bag processor includes a microcontroller for receiving the sensor signals and generating the measurement data.

11. The sleeping bag of claim 1, including adjustable vents to control air flow between an interior of the sleeping bag and the surrounding environment, wherein the vents include mesh, wherein the vents are integrated into the sleeping bag.

12. The sleeping bag system of claim 1, wherein the monitoring system includes:
    a temperature sensor assembly for a sleeping bag, the temperature sensor assembly including:
    a thermally conductive extension that protrudes from a waterproofing layer of the temperature sensor.

13. A method of using a sleeping bag system, the sleeping bag system including:
    a sleeping bag that is washable with water, including in a laundry machine, wherein the sleeping bag includes a monitoring system that includes:
    a plurality of sensors, including:
        at least one temperature sensor implanted into or onto fabric of the sleeping bag configured to measure an internal air temperature in the sleeping bag and/or a skin temperature of an occupant in the sleeping bag, and
        a movement sensor implanted into or onto the fabric of the sleeping bag to measure movement of the sleeping bag, wherein the movement sensor includes a plurality of strain sensors located in a first two-dimensional (2D) pattern on the front of the bag and a second 2D pattern on the back of the bag;
    electronic circuitry for the sensors located in the sleeping bag; and
    an enclosure that is removably attachable to the bag, the enclosure including:
    an on-bag processor,
    a wireless transceiver to communicate information represented by measurement data from sensor signals representing the measurements from the sensors, and
    a battery for powering the monitoring system,
    wherein the method includes using the plurality of sensors.

14. The method of claim 13, wherein using the plurality of sensors includes at least one of the following:
    (a) measuring an internal air temperature in the sleeping bag using the at least one temperature sensor;
    (b) measuring a skin temperature of the occupant in the sleeping bag; and
    (c) measuring movement of the sleeping bag using the plurality of strain sensors.

15. The method of claim 14, wherein the strain sensors measure movement of the sleeping bag by detecting changes in pressure on their surfaces.

16. The method of claim 13, wherein using the plurality of sensors includes the plurality of strain sensors located in the second 2D pattern on the back of the bag measuring the occupant's heart rate and/or respiration rate.

17. The method of claim 13, wherein using the plurality of sensors includes the plurality of strain sensors determining that the occupant is in an undesirable position.

18. The method of claim 17, further including:
in response to the plurality of strain sensors determining that the occupant is in an undesirable position, the system generating and sending an alert.

\* \* \* \* \*